(12) United States Patent
Uchida et al.

(10) Patent No.: US 11,726,099 B2
(45) Date of Patent: Aug. 15, 2023

(54) BIOMARKER FOR MENTAL DISORDERS INCLUDING COGNITIVE DISORDERS, AND METHOD USING SAID BIOMARKER TO DETECT MENTAL DISORDERS INCLUDING COGNITIVE DISORDERS

(71) Applicant: MCBI INC., Tsukuba (JP)

(72) Inventors: Kazuhiko Uchida, Tsukuba (JP); Takashi Ishi, Tsukuba (JP); Kohji Meno, Tsukuba (JP); Hideaki Suzuki, Tsukuba (JP)

(73) Assignee: MCBI INC., Tsukuba (JP)

( * ) Notice: Subject to any disclaimer, the term of this patent is extended or adjusted under 35 U.S.C. 154(b) by 0 days.

(21) Appl. No.: 16/539,829

(22) Filed: Aug. 13, 2019

(65) Prior Publication Data

US 2020/0057079 A1     Feb. 20, 2020

Related U.S. Application Data

(60) Continuation of application No. 14/263,645, filed on Apr. 28, 2014, now abandoned, which is a division of application No. 13/321,442, filed as application No. PCT/JP2010/003295 on May 17, 2010, now Pat. No. 8,748,574.

(51) Int. Cl.
*G01N 33/68*     (2006.01)
*C07K 14/47*     (2006.01)

(52) U.S. Cl.
CPC ......... *G01N 33/6896* (2013.01); *C07K 14/47* (2013.01); *G01N 2333/705* (2013.01); *G01N 2333/974* (2013.01); *G01N 2560/00* (2013.01); *G01N 2800/2814* (2013.01); *G01N 2800/2828* (2013.01)

(58) Field of Classification Search
CPC ......... G01N 33/6896; G01N 2333/705; G01N 2800/2828; C07K 14/47
See application file for complete search history.

(56) References Cited

U.S. PATENT DOCUMENTS

| 7,972,601 B2 | 7/2011 | Taylor et al. |
| 2002/0037528 A1 | 3/2002 | Berg et al. |
| 2007/0093443 A1 | 4/2007 | Madison et al. |
| 2008/0199426 A1 | 8/2008 | Sukhatme et al. |

FOREIGN PATENT DOCUMENTS

| JP | 2004-333274 A | 11/2004 |
| JP | 2006-308533 A | 11/2006 |
| WO | WO 01/12839 A1 | 2/2001 |
| WO | WO 02/088322 A2 | 11/2002 |
| WO | WO 03/087768 A2 | 10/2003 |
| WO | WO 2004/001421 A2 | 12/2003 |
| WO | WO 2004/019043 A2 | 3/2004 |
| WO | WO 2005/052592 A2 | 6/2005 |
| WO | WO 2006/035237 A2 | 4/2006 |
| WO | WO 2006/121952 A2 | 11/2006 |
| WO | WO 2007/045865 A2 | 4/2007 |
| WO | WO 2008/090319 A2 | 7/2008 |

OTHER PUBLICATIONS

Akiyama "Blood coagulation and fibrinolysis system in the brain of Alzheimer's disease patient," Dementia, vol. 9, 1995, pp. 124-131.
Benkirane et al, "Antigenicity and Immunogenicity of Modified Synthetic Peptides Containing D-Amino Acid Residues," The Journal of Biological Chemistry, vol. 268, No. 35, Dec. 15, 1993, pp. 26279-26285.
Chauhan et al, "Binding of Gelsolin, a Secretory Protein, to Amyloid B-Protein," Biochemical and Biophysical Research Communications., vol. 258, Apr. 1, 1999, pp. 241-246.
Extended European Search Report, dated Feb. 14, 2013, for European Application No. 10777546.2.
Hishimoto et al, "NRXNI: novel mRNA Transcripts, Differential Expression in and Association with Alzheimer Disease," Poster: Dementia & Cognitive Disorders, P-007, The World Journal of Biological Psychiatry, vol. 9, Supplement 1, 2008, p. 155.
Nakano et al, "The better understanding of Alzheimer's disease," Nagai Shoten Co., Ltd., 2004, p. 33, line 21-p. 34, line 24.
Südhof, "Neuroligins and neurexins link synaptic function to cognitive disease," Nature, vol. 455, Review Insight, Oct. 16, 2008, pp. 903-911.

*Primary Examiner* — Olga N Chernyshev
(74) *Attorney, Agent, or Firm* — Birch, Stewart, Kolasch & Birch, LLP

(57) ABSTRACT

Methods are provided that detect cognitive impairment including mild cognitive impairment and Alzheimer disease by using a protein or its partial peptide that differs in presence or absence. Novel biomarkers are also provided for cognitive impairment and non-psychiatric disease, as well as methods for detecting cognitive impairment using such biomarkers. Specifically, a biomarker for diagnosis is provided that comprises a protein fragment or peptide of not less than 5 amino acid residues arising from at least one protein or peptide selected from the group of proteins consisting of an amino acid sequence expressed by SEQ ID NO: 1, 3, 6, 8, 10, 13, 15, 18, or 20 and selected from the group of partial peptide in these proteins consisting of an amino acid sequence expressed by SEQ ID NO: 2, 4, 5, 7, 9, 11, 12, 14, 16, 17, 19, or 21.

3 Claims, 12 Drawing Sheets

Specification includes a Sequence Listing.

MCI vs ADN

AD vs ADN

AD vs NDnon

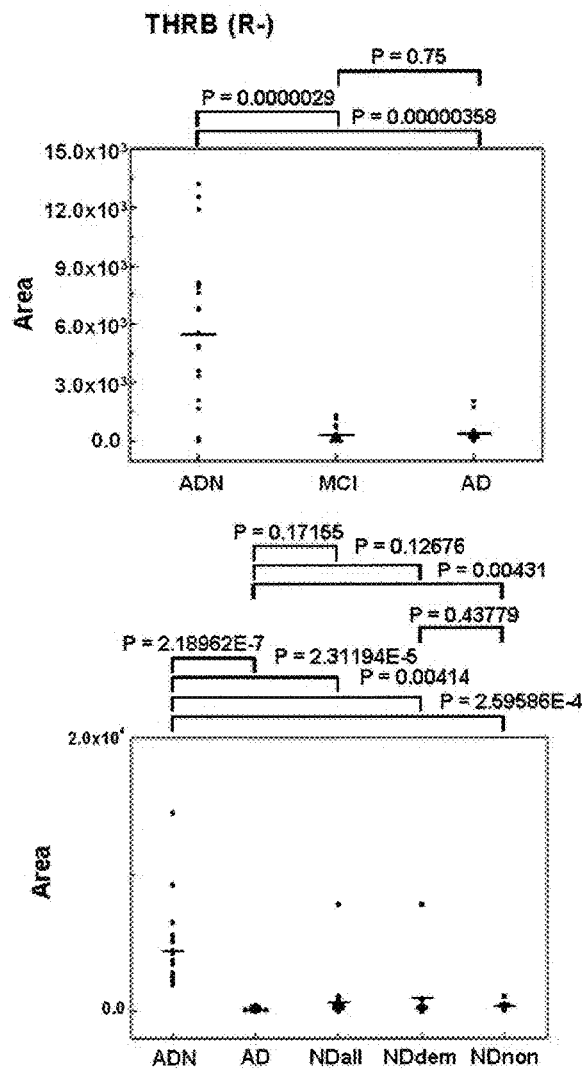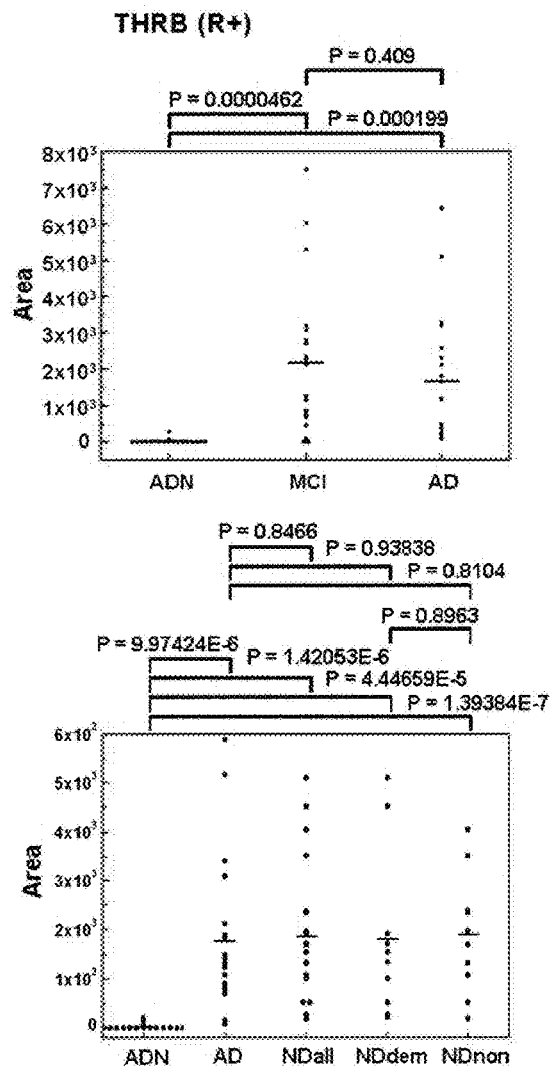
FIG. 4A    FIG. 4B)
FIG. 4C)   FIG. 4D)

FIG. 5A)
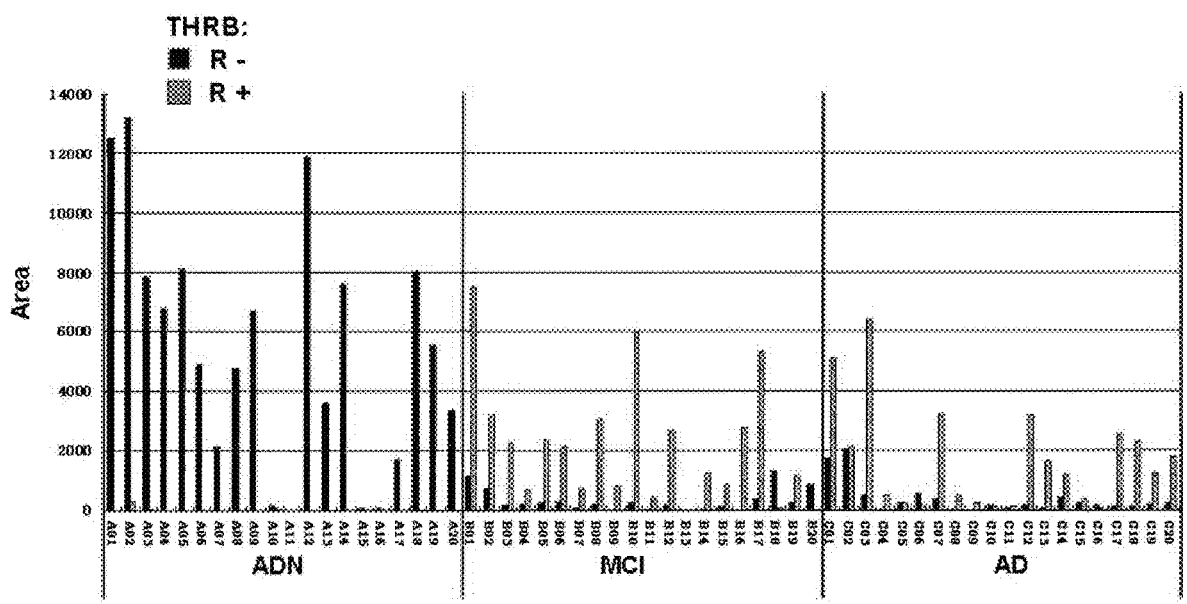
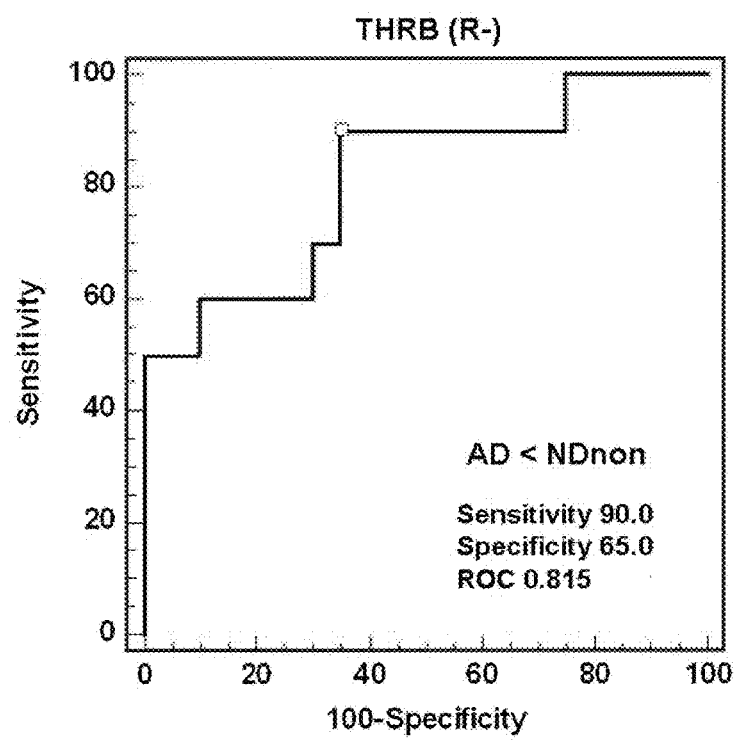
FIG. 5B)

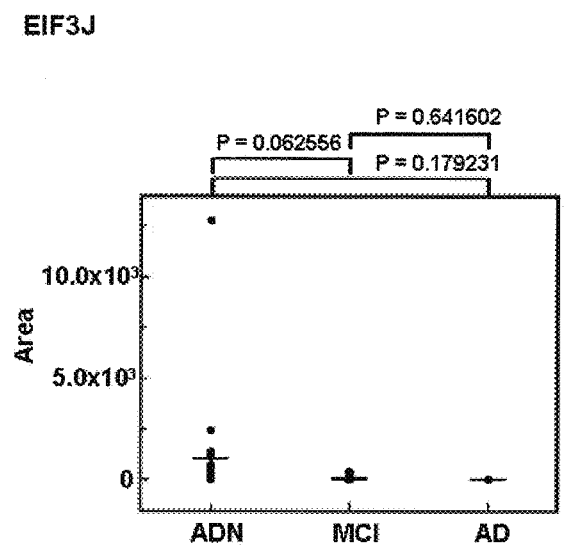
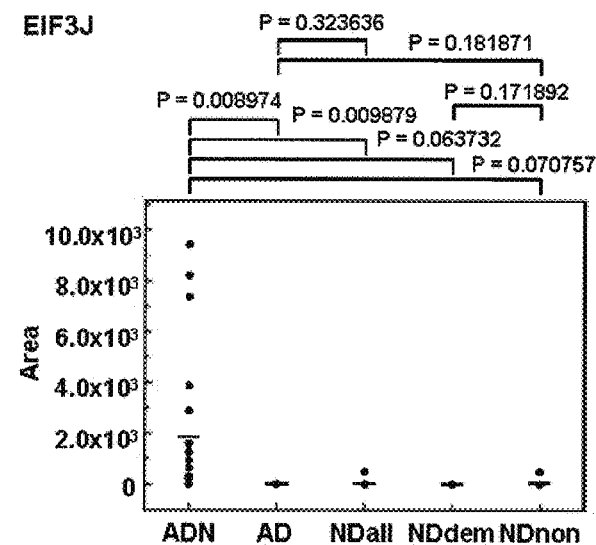
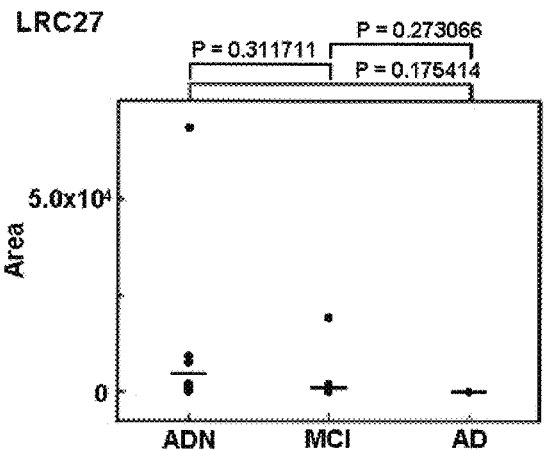

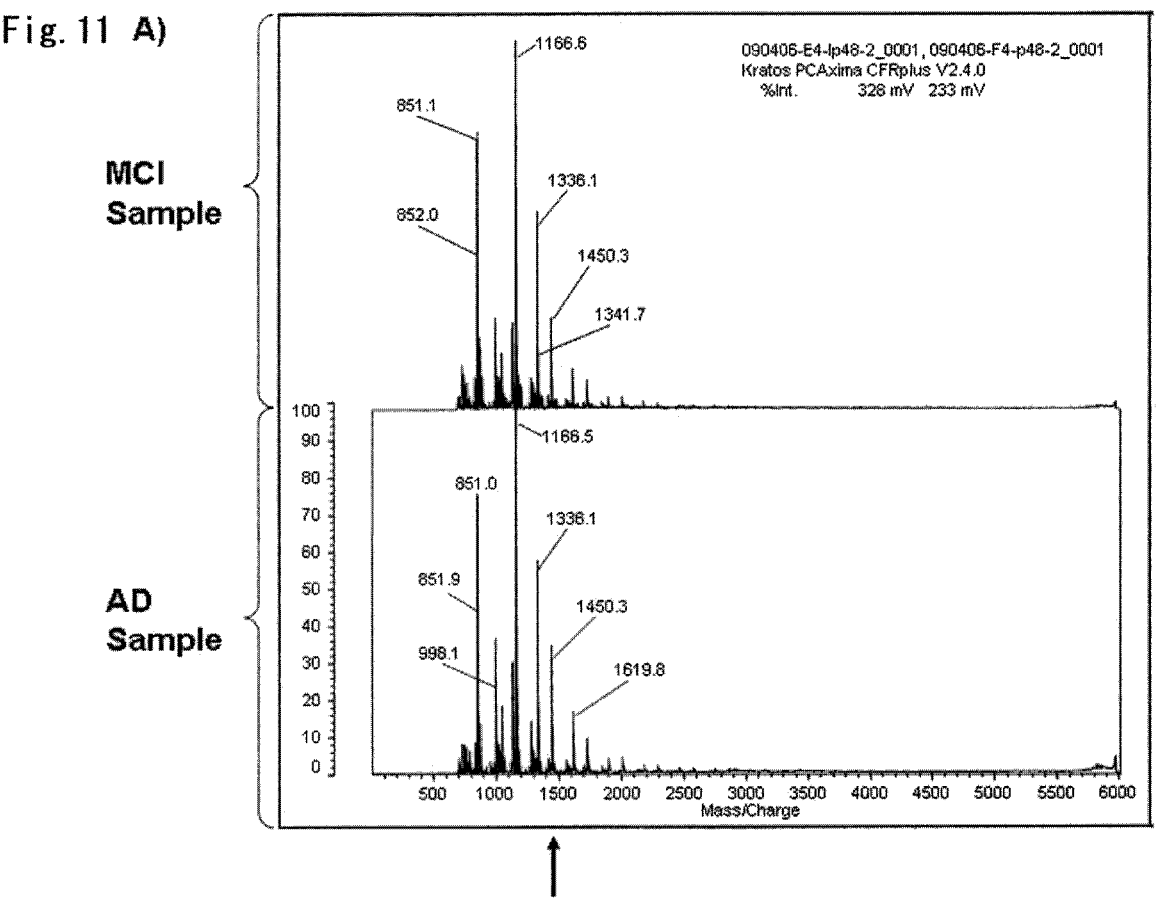

… (1) 기 …

SEQUENCE LISTING

```
<160> NUMBER OF SEQ ID NOS: 25

<210> SEQ ID NO 1
<211> LENGTH: 616
<212> TYPE: PRT
<213> ORGANISM: Homo sapiens

<400> SEQUENCE: 1

Met Pro Pro Gly Gly Ser Gly Pro Gly Gly Cys Pro Arg Arg Pro Pro
1               5                   10                  15

Ala Leu Ala Gly Pro Leu Pro Pro Pro Pro Pro Pro Pro Pro Pro Pro
                20                  25                  30

Leu Leu Pro Leu Leu Pro Leu Leu Leu Leu Leu Leu Leu Gly Ala Ala
            35                  40                  45

Glu Gly Ala Arg Val Ser Ser Ser Leu Ser Thr Thr His His Val His
    50                  55                  60

His Phe His Ser Lys His Gly Thr Val Pro Ile Ala Ile Asn Arg Met
65                  70                  75                  80

Pro Phe Leu Thr Arg Gly Gly His Ala Gly Thr Thr Tyr Ile Phe Gly
                85                  90                  95

Lys Gly Gly Ala Leu Ile Thr Tyr Thr Trp Pro Pro Asn Asp Arg Pro
            100                 105                 110

Ser Thr Arg Met Asp Arg Leu Ala Val Gly Phe Ser Thr His Gln Arg
    115                 120                 125

Ser Ala Val Leu Val Arg Val Asp Ser Ala Ser Gly Leu Gly Asp Tyr
        130                 135                 140

Leu Gln Leu His Ile Asp Gln Gly Thr Val Gly Val Ile Phe Asn Val
145                 150                 155                 160

Gly Thr Asp Asp Ile Thr Ile Asp Glu Pro Asn Ala Ile Val Ser Asp
                165                 170                 175
```

-continued

```
Gly Lys Tyr His Val Val Arg Phe Thr Arg Ser Gly Gly Asn Ala Thr
            180                 185                 190

Leu Gln Val Asp Ser Trp Pro Val Asn Glu Arg Tyr Pro Ala Gly Asn
        195                 200                 205

Phe Asp Asn Glu Arg Leu Ala Ile Ala Arg Gln Arg Ile Pro Tyr Arg
    210                 215                 220

Leu Gly Arg Val Val Asp Glu Trp Leu Leu Asp Lys Gly Arg Gln Leu
225                 230                 235                 240

Thr Ile Phe Asn Ser Gln Ala Ala Ile Lys Ile Gly Gly Arg Asp Gln
                245                 250                 255

Gly Arg Pro Phe Gln Gly Gln Val Ser Gly Leu Tyr Tyr Asn Gly Leu
            260                 265                 270

Lys Val Leu Ala Leu Ala Ala Glu Ser Asp Pro Asn Val Arg Thr Glu
        275                 280                 285

Gly His Leu Arg Leu Val Gly Glu Gly Pro Ser Val Leu Val Ala Ser
    290                 295                 300

Ala Glu Cys Pro Ser Asp Asp Glu Asp Leu Glu Glu Cys Glu Pro Ser
305                 310                 315                 320

Thr Gly Gly Glu Leu Ile Leu Pro Ile Ile Thr Glu Asp Ser Leu Asp
                325                 330                 335

Pro Pro Pro Val Ala Thr Arg Ser Pro Phe Val Pro Pro Pro Pro Thr
            340                 345                 350

Phe Tyr Pro Phe Leu Thr Gly Val Gly Ala Thr Gln Asp Thr Leu Pro
        355                 360                 365

Pro Pro Ala Ala Arg Arg Pro Pro Ser Gly Gly Pro Cys Gln Ala Glu
    370                 375                 380

Arg Asp Asp Ser Asp Cys Glu Glu Pro Ile Glu Ala Ser Gly Phe Ala
385                 390                 395                 400

Ser Gly Glu Val Phe Asp Ser Ser Leu Pro Pro Thr Asp Asp Glu Asp
                405                 410                 415

Phe Tyr Thr Thr Phe Pro Leu Val Thr Asp Arg Thr Thr Leu Leu Ser
            420                 425                 430

Pro Arg Lys Pro Ala Pro Arg Pro Asn Leu Arg Thr Asp Gly Ala Thr
        435                 440                 445

Gly Ala Pro Gly Val Leu Phe Ala Pro Ser Ala Pro Ala Pro Asn Leu
    450                 455                 460

Pro Ala Gly Lys Met Asn His Arg Asp Pro Leu Gln Pro Leu Leu Glu
465                 470                 475                 480

Asn Pro Pro Leu Gly Pro Gly Ala Pro Thr Ser Phe Glu Pro Arg Arg
                485                 490                 495

Pro Pro Pro Leu Arg Pro Gly Val Thr Ser Ala Pro Gly Phe Pro His
            500                 505                 510

Leu Pro Thr Ala Asn Pro Thr Gly Pro Gly Glu Arg Gly Pro Pro Gly
        515                 520                 525

Ala Val Glu Val Ile Arg Glu Ser Ser Ser Thr Thr Gly Met Val Val
    530                 535                 540

Gly Ile Val Ala Ala Ala Ala Leu Cys Ile Leu Ile Leu Leu Tyr Ala
545                 550                 555                 560

Met Tyr Lys Tyr Arg Asn Arg Asp Glu Gly Ser Tyr Gln Val Asp Gln
                565                 570                 575

Ser Arg Asn Tyr Ile Ser Asn Ser Ala Gln Ser Asn Gly Ala Val Val
            580                 585                 590
```

```
Lys Glu Lys Ala Pro Ala Ala Pro Lys Thr Pro Ser Lys Ala Lys Lys
            595                 600                 605

Asn Lys Asp Lys Glu Tyr Tyr Val
    610                 615

<210> SEQ ID NO 2
<211> LENGTH: 14
<212> TYPE: PRT
<213> ORGANISM: Homo sapiens

<400> SEQUENCE: 2

Arg Ser Gly Gly Asn Ala Thr Leu Gln Val Asp Ser Trp Pro
1               5                   10

<210> SEQ ID NO 3
<211> LENGTH: 622
<212> TYPE: PRT
<213> ORGANISM: Homo sapiens

<400> SEQUENCE: 3

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
    50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
    130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
    210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
        275                 280                 285
```

```
Asn Tyr Cys Glu Glu Ala Val Glu Glu Thr Gly Asp Gly Leu Asp
    290                 295                 300
Glu Asp Ser Asp Arg Ala Ile Glu Gly Arg Thr Ala Thr Ser Glu Tyr
305                 310                 315                 320
Gln Thr Phe Phe Asn Pro Arg Thr Phe Gly Ser Gly Glu Ala Asp Cys
                325                 330                 335
Gly Leu Arg Pro Leu Phe Glu Lys Lys Ser Leu Glu Asp Lys Thr Glu
            340                 345                 350
Arg Glu Leu Leu Glu Ser Tyr Ile Asp Gly Arg Ile Val Glu Gly Ser
        355                 360                 365
Asp Ala Glu Ile Gly Met Ser Pro Trp Gln Val Met Leu Phe Arg Lys
370                 375                 380
Ser Pro Gln Glu Leu Leu Cys Gly Ala Ser Leu Ile Ser Asp Arg Trp
385                 390                 395                 400
Val Leu Thr Ala Ala His Cys Leu Leu Tyr Pro Pro Trp Asp Lys Asn
                405                 410                 415
Phe Thr Glu Asn Asp Leu Leu Val Arg Ile Gly Lys His Ser Arg Thr
            420                 425                 430
Arg Tyr Glu Arg Asn Ile Glu Lys Ile Ser Met Leu Glu Lys Ile Tyr
        435                 440                 445
Ile His Pro Arg Tyr Asn Trp Arg Glu Asn Leu Asp Arg Asp Ile Ala
450                 455                 460
Leu Met Lys Leu Lys Lys Pro Val Ala Phe Ser Asp Tyr Ile His Pro
465                 470                 475                 480
Val Cys Leu Pro Asp Arg Glu Thr Ala Ala Ser Leu Leu Gln Ala Gly
                485                 490                 495
Tyr Lys Gly Arg Val Thr Gly Trp Gly Asn Leu Lys Glu Thr Trp Thr
            500                 505                 510
Ala Asn Val Gly Lys Gly Gln Pro Ser Val Leu Gln Val Val Asn Leu
        515                 520                 525
Pro Ile Val Glu Arg Pro Val Cys Lys Asp Ser Thr Arg Ile Arg Ile
530                 535                 540
Thr Asp Asn Met Phe Cys Ala Gly Tyr Lys Pro Asp Glu Gly Lys Arg
545                 550                 555                 560
Gly Asp Ala Cys Glu Gly Asp Ser Gly Gly Pro Phe Val Met Lys Ser
                565                 570                 575
Pro Phe Asn Asn Arg Trp Tyr Gln Met Gly Ile Val Ser Trp Gly Glu
            580                 585                 590
Gly Cys Asp Arg Asp Gly Lys Tyr Gly Phe Tyr Thr His Val Phe Arg
        595                 600                 605
Leu Lys Lys Trp Ile Gln Lys Val Ile Asp Gln Phe Gly Glu
610                 615                 620

<210> SEQ ID NO 4
<211> LENGTH: 12
<212> TYPE: PRT
<213> ORGANISM: Homo sapiens

<400> SEQUENCE: 4

Gly Leu Asp Glu Asp Ser Asp Arg Ala Ile Glu Gly
1               5                   10

<210> SEQ ID NO 5
<211> LENGTH: 13
<212> TYPE: PRT
<213> ORGANISM: Homo sapiens
```

-continued

<400> SEQUENCE: 5

Gly Leu Asp Glu Asp Ser Asp Arg Ala Ile Glu Gly Arg
1               5                   10

<210> SEQ ID NO 6
<211> LENGTH: 780
<212> TYPE: PRT
<213> ORGANISM: Homo sapiens

<400> SEQUENCE: 6

Met Ala Ala Pro Gly Gly Arg Ser Glu Pro Pro Gln Leu Pro Glu Tyr
1               5                   10                  15

Ser Cys Ser Tyr Met Val Ser Arg Pro Val Tyr Ser Glu Leu Ala Phe
                20                  25                  30

Gln Gln Gln His Glu Arg Arg Leu Gln Glu Arg Lys Thr Leu Arg Glu
            35                  40                  45

Ser Leu Ala Lys Cys Cys Ser Cys Ser Arg Lys Arg Ala Phe Gly Val
    50                  55                  60

Leu Lys Thr Leu Val Pro Ile Leu Glu Trp Leu Pro Lys Tyr Arg Val
65                  70                  75                  80

Lys Glu Trp Leu Leu Ser Asp Val Ile Ser Gly Val Ser Thr Gly Leu
                85                  90                  95

Val Ala Thr Leu Gln Gly Met Ala Tyr Ala Leu Leu Ala Ala Val Pro
                100                 105                 110

Val Gly Tyr Gly Leu Tyr Ser Ala Phe Phe Pro Ile Leu Thr Tyr Phe
            115                 120                 125

Ile Phe Gly Thr Ser Arg His Ile Ser Val Gly Pro Phe Pro Val Val
130                 135                 140

Ser Leu Met Val Gly Ser Val Val Leu Ser Met Ala Pro Asp Glu His
145                 150                 155                 160

Phe Leu Val Ser Ser Asn Gly Thr Val Leu Asn Thr Thr Met Ile
                165                 170                 175

Asp Thr Ala Ala Arg Asp Thr Ala Arg Val Leu Ile Ala Ser Ala Leu
                180                 185                 190

Thr Leu Leu Val Gly Ile Ile Gln Leu Ile Phe Gly Gly Leu Gln Ile
            195                 200                 205

Gly Phe Ile Val Arg Tyr Leu Ala Asp Pro Leu Val Gly Gly Phe Thr
210                 215                 220

Thr Ala Ala Ala Phe Gln Val Leu Val Ser Gln Leu Lys Ile Val Leu
225                 230                 235                 240

Asn Val Ser Thr Lys Asn Tyr Asn Gly Val Leu Ser Ile Ile Tyr Thr
                245                 250                 255

Leu Val Glu Ile Phe Gln Asn Ile Gly Asp Thr Asn Leu Ala Asp Phe
                260                 265                 270

Thr Ala Gly Leu Leu Thr Ile Val Val Cys Met Ala Val Lys Glu Leu
            275                 280                 285

Asn Asp Arg Phe Arg His Lys Ile Pro Val Pro Ile Pro Ile Glu Val
290                 295                 300

Ile Val Thr Ile Ile Ala Thr Ala Ile Ser Tyr Gly Ala Asn Leu Glu
305                 310                 315                 320

Lys Asn Tyr Asn Ala Gly Ile Val Lys Ser Ile Pro Arg Gly Phe Leu
                325                 330                 335

Pro Pro Glu Leu Pro Pro Val Ser Leu Phe Ser Glu Met Leu Ala Ala
                340                 345                 350

-continued

```
Ser Phe Ser Ile Ala Val Val Ala Tyr Ala Ile Ala Ser Val Gly
        355                 360                 365
Lys Val Tyr Ala Thr Lys Tyr Asp Tyr Thr Ile Asp Gly Asn Gln Glu
    370                 375                 380
Phe Ile Ala Phe Gly Ile Ser Asn Ile Phe Ser Gly Phe Phe Ser Cys
385                 390                 395                 400
Phe Val Ala Thr Thr Ala Leu Ser Arg Thr Ala Val Gln Glu Ser Thr
                405                 410                 415
Gly Gly Lys Thr Gln Val Ala Gly Ile Ile Ser Ala Ala Ile Val Met
                420                 425                 430
Ile Ala Ile Leu Ala Leu Gly Lys Leu Leu Glu Pro Leu Gln Lys Ser
            435                 440                 445
Val Leu Ala Ala Val Ile Ala Asn Leu Lys Gly Met Phe Met Gln
        450                 455                 460
Leu Cys Asp Ile Pro Arg Leu Trp Arg Gln Asn Lys Ile Asp Ala Val
465                 470                 475                 480
Ile Trp Val Phe Thr Cys Ile Val Ser Ile Ile Leu Gly Leu Asp Leu
                485                 490                 495
Gly Leu Leu Ala Gly Leu Ile Phe Gly Leu Leu Thr Val Val Leu Arg
                500                 505                 510
Val Gln Phe Pro Ser Trp Asn Gly Leu Gly Ser Ile Pro Ser Thr Asp
            515                 520                 525
Ile Tyr Lys Ser Thr Lys Asn Tyr Lys Asn Ile Glu Glu Pro Gln Gly
        530                 535                 540
Val Lys Ile Leu Arg Phe Ser Ser Pro Ile Phe Tyr Gly Asn Val Asp
545                 550                 555                 560
Gly Phe Lys Lys Cys Ile Lys Ser Thr Val Gly Phe Asp Ala Ile Arg
                565                 570                 575
Val Tyr Asn Lys Arg Leu Lys Ala Leu Arg Lys Ile Gln Lys Leu Ile
            580                 585                 590
Lys Ser Gly Gln Leu Arg Ala Thr Lys Asn Gly Ile Ile Ser Asp Ala
        595                 600                 605
Val Ser Thr Asn Asn Ala Phe Glu Pro Asp Glu Asp Ile Glu Asp Leu
    610                 615                 620
Glu Glu Leu Asp Ile Pro Thr Lys Glu Ile Glu Ile Gln Val Asp Trp
625                 630                 635                 640
Asn Ser Glu Leu Pro Val Lys Val Asn Val Pro Lys Val Pro Ile His
                645                 650                 655
Ser Leu Val Leu Asp Cys Gly Ala Ile Ser Phe Leu Asp Val Val Gly
                660                 665                 670
Val Arg Ser Leu Arg Val Ile Val Lys Glu Phe Gln Arg Ile Asp Val
            675                 680                 685
Asn Val Tyr Phe Ala Ser Leu Gln Asp Tyr Val Ile Glu Lys Leu Glu
        690                 695                 700
Gln Cys Gly Phe Phe Asp Asp Asn Ile Arg Lys Asp Thr Phe Phe Leu
705                 710                 715                 720
Thr Val His Asp Ala Ile Leu Tyr Leu Gln Asn Gln Val Lys Ser Gln
                725                 730                 735
Glu Gly Gln Gly Ser Ile Leu Glu Thr Ile Thr Leu Ile Gln Asp Cys
            740                 745                 750
```

```
Lys Asp Thr Leu Glu Leu Ile Glu Thr Glu Leu Thr Glu Glu Leu
            755                 760                 765

Asp Val Gln Asp Glu Ala Met Arg Thr Leu Ala Ser
    770                 775                 780

<210> SEQ ID NO 7
<211> LENGTH: 14
<212> TYPE: PRT
<213> ORGANISM: Homo sapiens

<400> SEQUENCE: 7

Leu Ala Gly Leu Ile Phe Gly Leu Leu Thr Val Val Leu Arg
1               5                   10

<210> SEQ ID NO 8
<211> LENGTH: 177
<212> TYPE: PRT
<213> ORGANISM: Homo sapiens

<400> SEQUENCE: 8

Met Glu Ala Leu Ile Leu Glu Pro Ser Leu Tyr Thr Val Lys Ala Ile
1               5                   10                  15

Leu Ile Leu Asp Asn Asp Gly Asp Arg Leu Phe Ala Lys Tyr Tyr Asp
            20                  25                  30

Asp Thr Tyr Pro Ser Val Lys Glu Gln Lys Ala Phe Glu Lys Asn Ile
        35                  40                  45

Phe Asn Lys Thr His Arg Thr Asp Ser Glu Ile Ala Leu Leu Glu Gly
    50                  55                  60

Leu Thr Val Val Tyr Lys Ser Ser Ile Asp Leu Tyr Phe Tyr Val Ile
65                  70                  75                  80

Gly Ser Ser Tyr Glu Asn Glu Leu Met Leu Met Ala Val Leu Asn Cys
                85                  90                  95

Leu Phe Asp Ser Leu Ser Gln Met Leu Arg Lys Asn Val Glu Lys Arg
            100                 105                 110

Ala Leu Leu Glu Asn Met Glu Gly Leu Phe Leu Ala Val Asp Glu Ile
        115                 120                 125

Val Asp Gly Gly Val Ile Leu Glu Ser Asp Pro Gln Gln Val Val His
    130                 135                 140

Arg Val Ala Leu Arg Gly Glu Asp Val Pro Leu Thr Glu Gln Thr Val
145                 150                 155                 160

Ser Gln Val Leu Gln Ser Ala Lys Glu Gln Ile Lys Trp Ser Leu Leu
                165                 170                 175

Arg

<210> SEQ ID NO 9
<211> LENGTH: 19
<212> TYPE: PRT
<213> ORGANISM: Homo sapiens

<400> SEQUENCE: 9

Ala Ile Leu Ile Leu Asp Asn Asp Gly Asp Arg Leu Phe Ala Lys Tyr
1               5                   10                  15

Tyr Asp Asp

<210> SEQ ID NO 10
<211> LENGTH: 163
<212> TYPE: PRT
<213> ORGANISM: Homo sapiens
```

<400> SEQUENCE: 10

Met Arg Arg Leu Leu Ile Pro Leu Ala Leu Trp Leu Gly Ala Val Gly
1               5                   10                  15

Val Gly Val Ala Glu Leu Thr Glu Ala Gln Arg Arg Gly Leu Gln Val
            20                  25                  30

Ala Leu Glu Glu Phe His Lys His Pro Pro Val Gln Trp Ala Phe Gln
        35                  40                  45

Glu Thr Ser Val Glu Ser Ala Val Asp Thr Pro Phe Pro Ala Gly Ile
    50                  55                  60

Phe Val Arg Leu Glu Phe Lys Leu Gln Gln Thr Ser Cys Arg Lys Arg
65                  70                  75                  80

Asp Trp Lys Lys Pro Glu Cys Lys Val Arg Pro Asn Gly Arg Lys Arg
                85                  90                  95

Lys Cys Leu Ala Cys Ile Lys Leu Gly Ser Glu Asp Lys Val Leu Gly
            100                 105                 110

Arg Leu Val His Cys Pro Ile Glu Thr Gln Val Leu Arg Glu Ala Glu
        115                 120                 125

Glu His Gln Glu Thr Gln Cys Leu Arg Val Gln Arg Ala Gly Glu Asp
    130                 135                 140

Pro His Ser Phe Tyr Phe Pro Gly Gln Phe Ala Phe Ser Lys Ala Leu
145                 150                 155                 160

Pro Arg Ser

<210> SEQ ID NO 11
<211> LENGTH: 18
<212> TYPE: PRT
<213> ORGANISM: Homo sapiens

<400> SEQUENCE: 11

Pro His Ser Phe Tyr Phe Pro Gly Gln Phe Ala Phe Ser Lys Ala Leu
1               5                   10                  15

Pro Arg

<210> SEQ ID NO 12
<211> LENGTH: 19
<212> TYPE: PRT
<213> ORGANISM: Homo sapiens

<400> SEQUENCE: 12

Pro His Ser Phe Tyr Phe Pro Gly Gln Phe Ala Phe Ser Lys Ala Leu
1               5                   10                  15

Pro Arg Ser

<210> SEQ ID NO 13
<211> LENGTH: 782
<212> TYPE: PRT
<213> ORGANISM: Homo sapiens

<400> SEQUENCE: 13

Met Ala Pro His Arg Pro Ala Pro Ala Leu Leu Cys Ala Leu Ser Leu
1               5                   10                  15

Ala Leu Cys Ala Leu Ser Leu Pro Val Arg Ala Ala Thr Ala Ser Arg
            20                  25                  30

Gly Ala Ser Gln Ala Gly Ala Pro Gln Gly Arg Val Pro Glu Ala Arg
        35                  40                  45

Pro Asn Ser Met Val Val Glu His Pro Glu Phe Leu Lys Ala Gly Lys
    50                  55                  60

-continued

```
Glu Pro Gly Leu Gln Ile Trp Arg Val Glu Lys Phe Asp Leu Val Pro
 65                  70                  75                  80
Val Pro Thr Asn Leu Tyr Gly Asp Phe Thr Gly Asp Ala Tyr Val
                 85                  90                  95
Ile Leu Lys Thr Val Gln Leu Arg Asn Gly Asn Leu Gln Tyr Asp Leu
                100                 105                 110
His Tyr Trp Leu Gly Asn Glu Cys Ser Gln Asp Glu Ser Gly Ala Ala
                115                 120                 125
Ala Ile Phe Thr Val Gln Leu Asp Asp Tyr Leu Asn Gly Arg Ala Val
            130                 135                 140
Gln His Arg Glu Val Gln Gly Phe Glu Ser Ala Thr Phe Leu Gly Tyr
145                 150                 155                 160
Phe Lys Ser Gly Leu Lys Tyr Lys Lys Gly Gly Val Ala Ser Gly Phe
                165                 170                 175
Lys His Val Val Pro Asn Glu Val Val Gln Arg Leu Phe Gln Val
                180                 185                 190
Lys Gly Arg Arg Val Val Arg Ala Thr Glu Val Pro Val Ser Trp Glu
                195                 200                 205
Ser Phe Asn Asn Gly Asp Cys Phe Ile Leu Asp Leu Gly Asn Asn Ile
    210                 215                 220
His Gln Trp Cys Gly Ser Asn Ser Asn Arg Tyr Glu Arg Leu Lys Ala
225                 230                 235                 240
Thr Gln Val Ser Lys Gly Ile Arg Asp Asn Glu Arg Ser Gly Arg Ala
                245                 250                 255
Arg Val His Val Ser Glu Glu Gly Thr Glu Pro Glu Ala Met Leu Gln
                260                 265                 270
Val Leu Gly Pro Lys Pro Ala Leu Pro Ala Gly Thr Glu Asp Thr Ala
                275                 280                 285
Lys Glu Asp Ala Ala Asn Arg Lys Leu Ala Lys Leu Tyr Lys Val Ser
            290                 295                 300
Asn Gly Ala Gly Thr Met Ser Val Ser Leu Val Ala Asp Glu Asn Pro
305                 310                 315                 320
Phe Ala Gln Gly Ala Leu Lys Ser Glu Asp Cys Phe Ile Leu Asp His
                325                 330                 335
Gly Lys Asp Gly Lys Ile Phe Val Trp Lys Gly Lys Gln Ala Asn Thr
                340                 345                 350
Glu Glu Arg Lys Ala Ala Leu Lys Thr Ala Ser Asp Phe Ile Thr Lys
            355                 360                 365
Met Asp Tyr Pro Lys Gln Thr Gln Val Ser Val Leu Pro Glu Gly Gly
370                 375                 380
Glu Thr Pro Leu Phe Lys Gln Phe Phe Lys Asn Trp Arg Asp Pro Asp
385                 390                 395                 400
Gln Thr Asp Gly Leu Gly Leu Ser Tyr Leu Ser Ser His Ile Ala Asn
                405                 410                 415
Val Glu Arg Val Pro Phe Asp Ala Ala Thr Leu His Thr Ser Thr Ala
                420                 425                 430
Met Ala Ala Gln His Gly Met Asp Asp Asp Gly Thr Gly Gln Lys Gln
            435                 440                 445
Ile Trp Arg Ile Glu Gly Ser Asn Lys Val Pro Val Asp Pro Ala Thr
            450                 455                 460
Tyr Gly Gln Phe Tyr Gly Gly Asp Ser Tyr Ile Ile Leu Tyr Asn Tyr
465                 470                 475                 480
```

```
Arg His Gly Gly Arg Gln Gly Gln Ile Ile Tyr Asn Trp Gln Gly Ala
            485                 490                 495

Gln Ser Thr Gln Asp Glu Val Ala Ala Ser Ala Ile Leu Thr Ala Gln
            500                 505                 510

Leu Asp Glu Glu Leu Gly Gly Thr Pro Val Gln Ser Arg Val Val Gln
            515                 520                 525

Gly Lys Glu Pro Ala His Leu Met Ser Leu Phe Gly Gly Lys Pro Met
530                 535                 540

Ile Ile Tyr Lys Gly Gly Thr Ser Arg Glu Gly Gln Thr Ala Pro
545                 550                 555                 560

Ala Ser Thr Arg Leu Phe Gln Val Arg Ala Asn Ser Ala Gly Ala Thr
            565                 570                 575

Arg Ala Val Glu Val Leu Pro Lys Ala Gly Ala Leu Asn Ser Asn Asp
            580                 585                 590

Ala Phe Val Leu Lys Thr Pro Ser Ala Ala Tyr Leu Trp Val Gly Thr
            595                 600                 605

Gly Ala Ser Glu Ala Glu Lys Thr Gly Ala Gln Glu Leu Leu Arg Val
            610                 615                 620

Leu Arg Ala Gln Pro Val Gln Val Ala Glu Gly Ser Glu Pro Asp Gly
625                 630                 635                 640

Phe Trp Glu Ala Leu Gly Gly Lys Ala Ala Tyr Arg Thr Ser Pro Arg
            645                 650                 655

Leu Lys Asp Lys Lys Met Asp Ala His Pro Pro Arg Leu Phe Ala Cys
            660                 665                 670

Ser Asn Lys Ile Gly Arg Phe Val Ile Glu Glu Val Pro Gly Glu Leu
            675                 680                 685

Met Gln Glu Asp Leu Ala Thr Asp Asp Val Met Leu Leu Asp Thr Trp
            690                 695                 700

Asp Gln Val Phe Val Trp Val Gly Lys Asp Ser Gln Glu Glu Glu Lys
705                 710                 715                 720

Thr Glu Ala Leu Thr Ser Ala Lys Arg Tyr Ile Glu Thr Asp Pro Ala
            725                 730                 735

Asn Arg Asp Arg Arg Thr Pro Ile Thr Val Val Lys Gln Gly Phe Glu
            740                 745                 750

Pro Pro Ser Phe Val Gly Trp Phe Leu Gly Trp Asp Asp Asp Tyr Trp
            755                 760                 765

Ser Val Asp Pro Leu Asp Arg Ala Met Ala Glu Leu Ala Ala
            770                 775                 780

<210> SEQ ID NO 14
<211> LENGTH: 12
<212> TYPE: PRT
<213> ORGANISM: Homo sapiens

<400> SEQUENCE: 14

Pro Val Arg Ala Ala Thr Ala Ser Arg Gly Ala Ser
1               5                   10

<210> SEQ ID NO 15
<211> LENGTH: 449
<212> TYPE: PRT
<213> ORGANISM: Homo sapiens
```

<400> SEQUENCE: 15

```
Met Met Lys Thr Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
            20                  25                  30

Glu Met Ser Asn Gln Gly Ser Lys Tyr Val Asn Lys Glu Ile Gln Asn
        35                  40                  45

Ala Val Asn Gly Val Lys Gln Ile Lys Thr Leu Ile Glu Lys Thr Asn
    50                  55                  60

Glu Glu Arg Lys Thr Leu Leu Ser Asn Leu Glu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly Arg Gln Leu Glu Glu Phe Leu
    130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
        195                 200                 205

Phe Ser Leu Pro His Arg Pro His Phe Phe Pro Lys Ser Arg
    210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
        275                 280                 285

Arg His Asn Ser Thr Gly Cys Leu Arg Met Lys Asp Gln Cys Asp Lys
    290                 295                 300

Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
                325                 330                 335

Leu Thr Arg Lys Tyr Asn Glu Leu Leu Lys Ser Tyr Gln Trp Lys Met
            340                 345                 350

Leu Asn Thr Ser Ser Leu Leu Glu Gln Leu Asn Glu Gln Phe Asn Trp
        355                 360                 365

Val Ser Arg Leu Ala Asn Leu Thr Gln Gly Glu Asp Gln Tyr Tyr Leu
    370                 375                 380

Arg Val Thr Thr Val Ala Ser His Thr Ser Asp Ser Asp Val Pro Ser
385                 390                 395                 400

Gly Val Thr Glu Val Val Val Lys Leu Phe Asp Ser Asp Pro Ile Thr
                405                 410                 415
```

-continued

Val Thr Val Pro Val Glu Val Ser Arg Lys Asn Pro Lys Phe Met Glu
            420                 425                 430

Thr Val Ala Glu Lys Ala Leu Gln Glu Tyr Arg Lys Lys His Arg Glu
        435                 440                 445

Glu

<210> SEQ ID NO 16
<211> LENGTH: 17
<212> TYPE: PRT
<213> ORGANISM: Homo sapiens

<400> SEQUENCE: 16

Ser Asp Val Pro Ser Gly Val Thr Glu Val Val Val Lys Leu Phe Asp
1               5                   10                  15

Ser

<210> SEQ ID NO 17
<211> LENGTH: 20
<212> TYPE: PRT
<213> ORGANISM: Homo sapiens

<400> SEQUENCE: 17

Arg Phe Phe Thr Arg Glu Pro Gln Asp Thr Tyr His Tyr Leu Pro Phe
1               5                   10                  15

Ser Leu Pro His
            20

<210> SEQ ID NO 18
<211> LENGTH: 258
<212> TYPE: PRT
<213> ORGANISM: Homo sapiens

<400> SEQUENCE: 18

Met Ala Ala Ala Ala Ala Ala Gly Asp Ser Asp Ser Trp Asp Ala
1               5                   10                  15

Asp Ala Phe Ser Val Glu Asp Pro Val Arg Lys Val Gly Gly Gly
                20                  25                  30

Thr Ala Gly Gly Asp Arg Trp Glu Gly Glu Asp Glu Asp Val
            35                  40                  45

Lys Asp Asn Trp Asp Asp Asp Asp Glu Lys Lys Glu Glu Ala Glu
        50                  55                  60

Val Lys Pro Glu Val Lys Ile Ser Glu Lys Lys Ile Ala Glu Lys
65                  70                  75                  80

Ile Lys Glu Lys Glu Arg Gln Gln Lys Lys Arg Gln Glu Glu Ile Lys
                85                  90                  95

Lys Arg Leu Glu Glu Pro Glu Glu Pro Lys Val Leu Thr Pro Glu Glu
            100                 105                 110

Gln Leu Ala Asp Lys Leu Arg Leu Lys Lys Leu Gln Glu Glu Ser Asp
        115                 120                 125

Leu Glu Leu Ala Lys Glu Thr Phe Gly Val Asn Asn Ala Val Tyr Gly
    130                 135                 140

Ile Asp Ala Met Asn Pro Ser Ser Arg Asp Asp Phe Thr Glu Phe Gly
145                 150                 155                 160

Lys Leu Leu Lys Asp Lys Ile Thr Gln Tyr Glu Lys Ser Leu Tyr Tyr
                165                 170                 175

Ala Ser Phe Leu Glu Val Leu Val Arg Asp Val Cys Ile Ser Leu Glu
            180                 185                 190

```
Ile Asp Asp Leu Lys Lys Ile Thr Asn Ser Leu Thr Val Leu Cys Ser
            195                 200                 205

Glu Lys Gln Lys Gln Glu Lys Gln Ser Lys Ala Lys Lys Lys Lys
    210                 215                 220

Gly Val Val Pro Gly Gly Gly Leu Lys Ala Thr Met Lys Asp Asp Leu
225                 230                 235                 240

Ala Asp Tyr Gly Gly Tyr Asp Gly Gly Tyr Val Gln Asp Tyr Glu Asp
            245                 250                 255

Phe Met

<210> SEQ ID NO 19
<211> LENGTH: 25
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Oxidation of Methionine

<400> SEQUENCE: 19

Gly Val Val Pro Gly Gly Gly Leu Lys Ala Thr Met Lys Asp Asp Leu
1               5                   10                  15

Ala Asp Tyr Gly Gly Tyr Asp Gly Gly
            20                  25

<210> SEQ ID NO 20
<211> LENGTH: 530
<212> TYPE: PRT
<213> ORGANISM: Homo sapiens

<400> SEQUENCE: 20

Met Glu Gly Ser Ser Ser Tyr Glu Val Pro Ser Val Ala Ala Ala Asp
1               5                   10                  15

Leu Glu Glu Gly Ala Gly Gln Thr Arg Ser Leu Pro Ala Thr Pro Ser
            20                  25                  30

Lys Asp Val His Lys Gly Val Gly Gly Ile Ile Phe Ser Ser Ser Pro
        35                  40                  45

Ile Leu Asp Leu Ser Glu Ser Gly Leu Cys Arg Leu Glu Glu Val Phe
    50                  55                  60

Arg Ile Pro Ser Leu Gln Gln Leu His Leu Gln Arg Asn Ala Leu Cys
65                  70                  75                  80

Val Ile Pro Gln Asp Phe Phe Gln Leu Leu Pro Asn Leu Thr Trp Leu
            85                  90                  95

Asp Leu Arg Tyr Asn Arg Ile Lys Ala Leu Pro Ser Gly Ile Gly Ala
            100                 105                 110

His Gln His Leu Lys Thr Leu Leu Leu Glu Arg Asn Pro Ile Lys Met
        115                 120                 125

Leu Pro Val Glu Leu Gly Ser Val Thr Thr Leu Lys Ala Leu Asn Leu
    130                 135                 140

Arg His Cys Pro Leu Glu Phe Pro Pro Gln Leu Val Gln Lys Gly
145                 150                 155                 160

Leu Val Ala Ile Gln Arg Phe Leu Arg Met Trp Ala Val Glu His Ser
            165                 170                 175

Leu Pro Arg Asn Pro Thr Ser Gln Glu Ala Pro Val Arg Glu Met
        180                 185                 190

Thr Leu Arg Asp Leu Pro Ser Pro Gly Leu Glu Leu Ser Gly Asp His
    195                 200                 205
```

-continued

```
Ala Ser Asn Gln Gly Ala Val Asn Ala Gln Asp Pro Glu Gly Ala Val
    210                 215                 220
Met Lys Glu Lys Ala Ser Phe Leu Pro Pro Val Glu Lys Pro Asp Leu
225                 230                 235                 240
Ser Glu Leu Arg Lys Ser Ala Asp Ser Glu Asn Trp Pro Ser Glu
        245                 250                 255
Glu Glu Ile Arg Arg Phe Trp Lys Leu Arg Gln Glu Ile Val Glu His
                260                 265                 270
Val Lys Ala Asp Val Leu Gly Asp Gln Leu Leu Thr Arg Glu Leu Pro
            275                 280                 285
Pro Asn Leu Lys Ala Ala Leu Asn Ile Glu Lys Glu Leu Pro Lys Pro
    290                 295                 300
Arg His Val Phe Arg Arg Lys Thr Ala Ser Ser Arg Ser Ile Leu Pro
305                 310                 315                 320
Asp Leu Leu Ser Pro Tyr Gln Met Ala Ile Arg Ala Lys Arg Leu Glu
                325                 330                 335
Glu Ser Arg Ala Ala Ala Leu Arg Glu Leu Gln Glu Lys Gln Ala Leu
            340                 345                 350
Met Glu Gln Gln Arg Arg Glu Lys Arg Ala Leu Gln Glu Trp Arg Glu
    355                 360                 365
Arg Ala Gln Arg Met Arg Lys Arg Lys Glu Glu Leu Ser Lys Leu Leu
370                 375                 380
Pro Pro Arg Arg Ser Met Val Ala Ser Lys Ile Pro Ser Ala Thr Asp
385                 390                 395                 400
Leu Ile Asp Asn Arg Lys Val Pro Leu Asn Pro Pro Gly Lys Met Lys
                405                 410                 415
Pro Ser Lys Glu Lys Ser Pro Gln Ala Ser Lys Glu Met Ser Ala Leu
            420                 425                 430
Gln Glu Arg Asn Leu Glu Glu Lys Ile Lys Gln His Val Leu Gln Met
    435                 440                 445
Arg Glu Gln Arg Arg Phe His Gly Gln Ala Pro Leu Glu Glu Met Arg
450                 455                 460
Lys Ala Ala Glu Asp Leu Glu Ile Ala Thr Glu Leu Gln Asp Glu Val
465                 470                 475                 480
Leu Lys Leu Lys Leu Gly Leu Thr Leu Asn Lys Asp Arg Arg Ala
                485                 490                 495
Ala Leu Thr Gly Asn Leu Ser Leu Gly Leu Pro Ala Ala Gln Pro Gln
            500                 505                 510
Asn Thr Phe Phe Asn Thr Lys Tyr Gly Glu Ser Gly Asn Val Arg Arg
    515                 520                 525
Tyr Gln
    530

<210> SEQ ID NO 21
<211> LENGTH: 23
<212> TYPE: PRT
<213> ORGANISM: Homo sapiens

<400> SEQUENCE: 21

Ser Ser Pro Ile Leu Asp Leu Ser Glu Ser Gly Leu Cys Arg Leu Glu
1               5                   10                  15

Glu Val Phe Arg Ile Pro Ser
            20
```

```
<210> SEQ ID NO 22
<211> LENGTH: 8
<212> TYPE: PRT
<213> ORGANISM: Homo sapiens

<400> SEQUENCE: 22

Arg Ser Gly Gly Asn Ala Thr Cys
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic

<400> SEQUENCE: 23

Ile Arg Gly Glu Arg Ala
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic

<400> SEQUENCE: 24

Ile Lys Gly Glu Arg Ala
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic

<400> SEQUENCE: 25

Cys Gly Gly Gly Glu Arg Ala
1               5
```

BIOMARKER FOR MENTAL DISORDERS INCLUDING COGNITIVE DISORDERS, AND METHOD USING SAID BIOMARKER TO DETECT MENTAL DISORDERS INCLUDING COGNITIVE DISORDERS

This application is a Continuation of application Ser. No. 14/263,645 filed on Apr. 28, 2014, which is a Divisional of application Ser. No. 13/321,442 filed on Jan. 20, 2012 (now U.S. Pat. No. 8,748,574 B2 issued Jun. 10, 2014). Application Ser. No. 13/321,442 is a National Phase of PCT International Application No. PCT/JP2010/003295 filed on May 17, 2010, which claims the benefit of Japanese Application No. 2009-121226 filed on May 19, 2009. The entire contents of all of the above applications are hereby incorporated by reference.

REFERENCE TO SEQUENCE LISTING SUBMITTED VIA EFS-WEB

This application includes an electronically submitted sequence listing in .txt format. The .txt file contains a sequence listing entitled "2022-03-13_4877-0110PUS3_ST25.txt" created on Jan. 19, 2022 and is 41,982 bytes in size. The sequence listing contained in this .txt file is part of the specification and is hereby incorporated by reference herein in its entirety.

TECHNICAL FIELD

The present invention relates to novel biomarkers for cognitive impairment including mild cognitive impairment and Alzheimer disease and methods for detecting cognitive impairment using such biomarkers. Simultaneously, the present invention relates to novel biomarkers for non-demented neurological disease like depression, schizophrenia, etc. and methods for detecting non-demented neurological disease using such biomarkers.

BACKGROUND ART

The commonly used means to differentiate between normal and non-normal states of a human subject using his or her biological materials are mainly those which have been used in the field of diagnostics. Most frequently used are those methods which target biomarkers in blood. It has been practiced in this field to comparatively measure the amount of a specific protein or a peptide that is less than 10,000 in molecular weight or, in the case of enzyme protein, enzyme activities in samples from normal (healthy) subjects and those from diseased individuals to help diagnosis. Here, prior to testing real samples, measurements are done on a fixed number each of samples from healthy controls and patients with certain disease with respect to the amount (s) or activity (activities) of single or multiple specific proteins or peptides and the ranges of abnormal and normal values are respectively determined. The sample to be evaluated is then analyzed by the same method and the resultant value is judged with respect to whether it is in normal or in abnormal range.

In the actual measurements, the amount(s) of specified protein(s) or peptide(s) in test samples, as such or after dilution, are determined by the use of enzyme-linked immunosorbent assay (ELISA) which uses a primary, or secondary, antibody labeled with an enzyme reacting with a substrate that yields a color upon reaction, chemiluminescent immunoassay (CLIA), radioimmunoassay (RIA) which uses a primary, or secondary, antibody labeled with a radioisotope, and, if the protein is an enzyme, the measurement of the activity of the enzyme by adding its substrate and determining the intensity of produced color, etc. These antibody-based methods are called as enzyme-, fluorescence- or radioisotope-labeled methods, respectively. In addition, there is a method where an enzyme reaction product derived from the corresponding substrate is determined by high performance liquid chromatography (HPLC). In further addition, there is a method where HPLC is combined with mass spectrometer, called LC-MS/MS, and there is a method called selected reaction monitoring (SRM)/multiple reaction monitoring (MRM) that utilizes LC-MS/MS. In another method to determine the concentration in a sample, it is appropriately pretreated, and separation of proteins or peptides is attained by 2-dimensional polyacrylamide gel electrophoresis (2D-PAGE), and target protein or peptide is determined by silver staining, Coomassie blue staining or immunological staining (Western blotting) that uses an antibody to target protein or peptide. In still further addition, there is a method which utilizes mass spectrometry to determine the amount of target protein or peptide in samples fractionated by column chromatography. Instead of column chromatography, protein chips and magnetic beads may also be utilized for purpose of pretreatment.

Furthermore, these inventors have developed an immunoMS method, where target protein or peptide is captured by beads (including magnetic ones) with linked antibody to the protein or peptide, eluted from the beads, and determined by mass spectrometry. Further, intact proteins have been reported to be analyzed by mass spectrometry using abovementioned methods after digestion with trypsin etc. (PTL 1). Here, intact target proteins are selected either by fractionation or by adsorption to an adsorbant specific to them and then determined by mass spectrometry.

Number of patients suffered from cognitive impairment like Alzheimer disease is increasing rapidly along with increasing of old-age population in Japan. It is estimated that number of patients is 1.3 million in 1995 and it will be 1.9 million in 2005 and will reach to about 3.0 million in 2020. It is reported that 60-90% of cognitive impairment is Alzheimer disease. As manifestation of Alzheimer disease is not only loss of memory but several disturbance in daily life, increase of patients of this disease is becoming an important social issue to be solved. In Japan, Donepezil-hydrochloride, anti-acetylcholine esterase inhibitor has been available for medical treatment for Alzheimer disease since 1999, and it let progress of cognitive impairment in these patients be 'slow-down' efficiently, if the patient is diagnosed at early stage. Thus, in medication of Alzheimer disease, most important issue is 'early diagnosis' to treat the patients effectively by drug available at present and new coming drug.

Followings are major criteria for diagnosis of Alzheimer disease described in DSM-IV, which is published by American Psychiatric Association (Non-patent reference 1).

A. The development of multiple cognitive deficits manifested by both
  (1) memory impairment (impaired ability to learn new information or to recall previously learned information)
  (2) one (or more) of the following cognitive disturbances:
    a) aphasia (language disturbance)
    b) apraxia (impaired ability to carry out motor activities despite intact motor function)

c) agnosia (failure to recognize or identify objects despite intact sensory function)
d) disturbance in executive functioning (i.e., planning, organizing, sequencing, abstracting)

B. The cognitive deficits in Criteria A 1 and A2 each cause significant impairment in social or occupational functioning and represent a significant decline from a previous level of functioning.

There are several types of neurological disorders related to Alzheimer disease (AD). As cognitive dysfunction appears gradually in dementia including AD, there is a disease status of pre-stage of dementia. This stage is called as mild cognitive impairment (MCI). In United States, 10% MCI develops to AD within 1 year, and 50% of MCI develops to AD within 4 years. MCI is defined as a condition characterized by newly acquired cognitive decline to an extent that is beyond that expected for age or educational background, yet not causing significant functional impairment, and not showing disturbance in daily life. Frontotemporal dementia (frontotemporal lobar degeneration) (FTD) shows loss of personal awareness, loss of social awareness, hyperorality, and stereotyped, perseverative behavior. These clinical characteristics are different from AD. FTD includes Pick's disease, which is characterized by microscopically Pick bodies usually found in limbic, paralimbic, and ventral temporal lobe cortex. Dementia with Lewy bodies (DLB) is characterized by progressive disease and psychiatric symptoms include anxiety, depression, hallucinations (usually visual) and delusions (false beliefs). DLB is thought to be the second most common subtype and 10-30% of dementia is DLB. The symptoms of DLB are caused by the build-up of Lewy bodies histologically. FTD and DLB belong to demented neurological disease as they also lose of memory, their ability to solve problems and maintain emotional control (NPL 1). In description in present patent, cognitive impairment includes AD, MCI and the demented neurological disease.

The screening tests for dementia widely used are the Hasegawa Dementia Scale-revised (HDS-R) and Mini-Mental State Examination (MMSE). In these screening tests, inspector asks several questions and evaluates level of cognitive impairment of each subject by scores. HDS-R is revised version of HDS published in 1991. In HDS-R, test consists 9 questions to analyses orientation, remembrance, calculation, retain and recall ability, and common sense. Full score is 30 and a person whose score is less than 23 is suspected as dementia. MMSE has been developed in United States to screen and diagnose dementia, and analyses global cognitive function, with items assessing orientation, word recall, attention and calculation, language abilities, and visuospatial (drawing) ability. This test consists of 11 questions, and full score is 30 and a person who has score less than 23 is suspected as dementia. The results of HDS-R and MMSE coincide with each other. Both are used for screening, not for diagnosis and not for staging of disease progression (NPL 1).

Neuroimaging test for dementia are Computed tomography (CT) and Magnetic resonance imaging (MRI) which evaluate morphological changes like brain atrophy and ventricular dilation and single-photon emission computed tomography (SPECT) which analyses regional cerebral blood flow and PET which shows brain metabolism by measurement of consumption of oxygen and sugar. SPECT and PET, nuclear imaging technologies, can identify neuronal dysfunction at preclinical stage (NPL 1). However, these neuroimaging cannot be widely used in hospitals because they need special facilities to perform nuclear imaging, and neuroimaging may not be objective test as imaging diagnosis is completely depend on the skill of physician who analyses the mages.

Thus, methods for screening and diagnosis of dementia including AD that are available at present is dependent on tests lacking objectivity and is dependent on expensive instruments, and so it is very difficult to use these tests for screening of early stage-cognitive impairment. If we get blood (serum/plasma) biomarker for cognitive impairment, which enables us objective test using specimens we can easily obtain, we can identify cognitive impairment at early stage (preclinical stage) by blood test using such biomarker. Present patent provides novel biomarkers and a novel and potent diagnostic method for cognitive impairment by using such biomarkers and biomarkers described here. In addition, present patent provides diagnostic method and novel biomarkers for non-demented neurological disease like depression, schizophrenia, etc.

CITATION LIST

Patent Literature

PTL 1, JP-A-2004-333274
PTL 2, JP-A-2006-308533

Non Patent Literature

NPL 1, "Alzheimer's disease's textbook," edited by Imaharu Nakano and Hidehiro Mizusawa, Nagai Shoten Co., Ltd., 2004 (in Japanese)
NPL 2, Benkirane, N. et al., J. Biol. Chem. Vol. 268, 26279-26285, 1993

SUMMARY OF INVENTION

Technical Problem

The present invention aims to present methods to detect cognitive impairment including mild cognitive impairment and Alzheimer disease by using a protein or its partial peptide that differs in presence or absence, or in quantity between non-cognitive impairment subjects (Including healthy people, the human subjects that may be affected with any disease and unaffected with cognitive impairment) and patients with cognitive impairment and further aims to present biomarkers comprising said proteins and said partial peptides to be used to detect cognitive impairment including mild cognitive impairment and Alzheimer disease. Simultaneously, the present invention aims to present novel biomarkers for non-demented neurological disease like depression, schizophrenia, etc. and methods for detecting cognitive impairment using such biomarkers.

Solution to Problem

These inventors investigated to find out means to detect cognitive impairment and found a peptide capable of detecting cognitive impairment and psychiatric disease including mild cognitive impairment and Alzheimer disease in the serum. Said peptides found in the present invention are those with significance as a biomarker to detecting in the case of serum not only other biological materials such as blood, plasma, cerebrospinal fluid, and urine. Simultaneously, protein or peptide is the origin of these peptides (hereinafter referred to as intact proteins or peptides) also has significance as biomarkers.

Specifically, these inventors found that a biomarker comprising at least one protein or peptide selected from the group consisting of Neurexin-2-beta precursor consisting of amino acid sequence expressed by SEQ ID NO: 1, Prothrombin precursor consisting of amino acid sequence expressed by SEQ ID NO: 3, Pendrin consisting of amino acid sequence expressed by SEQ ID NO: 6, Coatomer subunit zeta-1 consisting of amino acid sequence expressed by SEQ ID NO: 8, Retinoic acid receptor responder protein 2 precursor consisting of amino acid sequence expressed by SEQ ID NO: 10, Gelsolin precursor consisting of amino acid sequence expressed by SEQ ID NO: 13, Clusterin precursor consisting of amino acid sequence expressed by SEQ ID NO: 15, Eukaryotic translation initiation factor 3 subunit J consisting of amino acid sequence expressed by SEQ ID NO: 18, and Leucine-rich repeat-containing protein 27 consisting of amino acid sequence expressed by SEQ ID NO: 20 could be used as biomarkers to detect psychiatric disease or cognitive impairment.

Furthermore, these inventors found that a biomarker comprising at least one peptide selected from the group consisting of Neurexin-2-beta precursor-derived peptide NRX2B consisting of amino acid sequence expressed by SEQ ID NO: 2, Prothrombin precursor-derived peptide THRB(R−) consisting of amino acid sequence expressed by SEQ ID NO: 4, Prothrombin precursor-derived peptide THRB(R+) consisting of amino acid sequence expressed by SEQ ID NO: 5, Pendrin-derived peptide S26A4 consisting of amino acid sequence expressed by SEQ ID NO: 7, Coatomer subunit zeta-1-derived peptide COPZ1 consisting of amino acid sequence expressed by SEQ ID NO: 9, Retinoic acid receptor responder protein 2 precursor-derived peptide RARR2(S−) consisting of amino acid sequence expressed by SEQ ID NO: 11, Retinoic acid receptor responder protein 2 precursor-derived peptide RARR2(S+) consisting of amino acid sequence expressed by SEQ ID NO: 12, Gelsolin precursor-derived peptide GELS consisting of amino acid sequence expressed by SEQ ID NO: 14, Clusterin precursor-derived peptide CLUS(N-term SDVP) consisting of amino acid sequence expressed by SEQ ID NO: 16, Clusterin precursor-derived peptide CLUS(N-term RFFT) consisting of amino acid sequence expressed by SEQ ID NO: 17, Eukaryotic translation initiation factor 3 subunit J-derived peptide EIF3J consisting of amino acid sequence expressed by SEQ ID NO: 19, and Leucine-rich repeat-containing protein 27-derived peptide LRC27 consisting of amino acid sequence expressed by SEQ ID NO: 21 could be used as biomarkers to detect psychiatric disease or cognitive impairment.

These inventors brought the present invention to perfection by further succeeding in determining simultaneously these many proteins and its partial peptides by using two-dimensional high performance liquid chromatography-MALDI TOFMS method (mass spectrometry) and immunoMS method.

The features of the present invention are shown below.

[1] A biomarker for detection of psychiatric disease or cognitive impairment comprising protein fragment or peptide of not less than 5 amino acid residues arising from at least one protein or peptide selected from the group consisting of Neurexin-2-beta precursor consisting of amino acid sequence expressed by SEQ ID NO: 1, Prothrombin precursor consisting of amino acid sequence expressed by SEQ ID NO: 3, Pendrin consisting of amino acid sequence expressed by SEQ ID NO: 6, Coatomer subunit zeta-1 consisting of amino acid sequence expressed by SEQ ID NO: 8, Retinoic acid receptor responder protein 2 precursor consisting of amino acid sequence expressed by SEQ ID NO: 10, Gelsolin precursor consisting of amino acid sequence expressed by SEQ ID NO: 13, Clusterin precursor consisting of amino acid sequence expressed by SEQ ID NO: 15, Eukaryotic translation initiation factor 3 subunit J consisting of amino acid sequence expressed by SEQ ID NO: 18, Leucine-rich repeat-containing protein 27 consisting of amino acid sequence expressed by SEQ ID NO: 20.

[2] A biomarker for detection of psychiatric disease comprising at least one peptide selected from the group consisting of Neurexin-2-beta precursor-derived peptide NRX2B consisting of amino acid sequence expressed by SEQ ID NO: 2, Prothrombin precursor-derived peptide THRB(R−) consisting of amino acid sequence expressed by SEQ ID NO: 4, Prothrombin precursor-derived peptide THRB(R+) consisting of amino acid sequence expressed by SEQ ID NO: 5, Pendrin-derived peptide S26A4 consisting of amino acid sequence expressed by SEQ ID NO: 7, Coatomer subunit zeta-1-derived peptide COPZ1 consisting of amino acid sequence expressed by SEQ ID NO: 9, Retinoic acid receptor responder protein 2 precursor-derived peptide RARR2(S−) consisting of amino acid sequence expressed by SEQ ID NO: 11, Retinoic acid receptor responder protein 2 precursor-derived peptide RARR2(S+) consisting of amino acid sequence expressed by SEQ ID NO: 12, Gelsolin precursor-derived peptide GELS consisting of amino acid sequence expressed by SEQ ID NO: 14, Clusterin precursor-derived peptide CLUS(N-term SDVP) consisting of amino acid sequence expressed by SEQ ID NO: 16, Clusterin precursor-derived peptide CLUS(N-term RFFT) consisting of amino acid sequence expressed by SEQ ID NO: 17, Eukaryotic translation initiation factor 3 subunit J-derived peptide EIF3J consisting of amino acid sequence expressed by SEQ ID NO: 19, and Leucine-rich repeat-containing protein 27-derived peptide LRC27 consisting of amino acid sequence expressed by SEQ ID NO: 21.

[3] A biomarker for detection of cognitive impairment comprising at least one peptide selected from the group consisting of Neurexin-2-beta precursor-derived peptide NRX2B consisting of amino acid sequence expressed by SEQ ID NO: 2, Prothrombin precursor-derived peptide THRB(R−) consisting of amino acid sequence expressed by SEQ ID NO: 4, Prothrombin precursor-derived peptide THRB(R+) consisting of amino acid sequence expressed by SEQ ID NO: 5, Pendrin-derived peptide S26A4 consisting of amino acid sequence expressed by SEQ ID NO: 7, Coatomer subunit zeta-1-derived peptide COPZ1 consisting of amino acid sequence expressed by SEQ ID NO: 9, Retinoic acid receptor responder protein 2 precursor-derived peptide RARR2(S−) consisting of amino acid sequence expressed by SEQ ID NO: 11, Retinoic acid receptor responder protein 2 precursor-derived peptide RARR2(S+) consisting of amino acid sequence expressed by SEQ ID NO: 12, Gelsolin precursor-derived peptide GELS consisting of amino acid sequence expressed by SEQ ID NO: 14, Clusterin precursor-derived peptide CLUS(N-term SDVP) consisting of amino acid sequence expressed by SEQ ID NO: 16, Clusterin precursor-derived peptide CLUS(N-term RFFT) consisting of amino acid sequence expressed by SEQ ID NO: 17, Eukaryotic translation initiation factor 3 subunit J-derived peptide EIF3J consisting of amino acid sequence expressed by SEQ ID NO: 19, and Leucine-rich repeat-containing protein 27-derived peptide LRC27 consisting of amino acid sequence expressed by SEQ ID NO: 21.

[4] A biomarker of cognitive impairment comprising the peptides selected from the group consisting of amino acid sequence expressed by SEQ ID NO: 2, 5, 7, 9, 11, 12, 14, and 16 that is appeared or increased in biological material of patients of cognitive impairment as compared to biological material of subjects not suffering from psychiatric disease.

[5] A biomarker of cognitive impairment comprising the peptides selected from the group consisting of amino acid sequence expressed by SEQ ID NO: 4, 17, 19, and 21 that is disappeared or decreased in biological material of patients of cognitive impairment as compared to biological material of subjects not suffering from psychiatric disease.

[6] A biomarker of Alzheimer disease comprising the peptides selected from the group consisting of amino acid sequence expressed by SEQ ID NO: 2 that is appeared or increased in biological material of patients of Alzheimer disease as compared to biological material of subjects not suffering from non-demented neurological disease.

[7] A biomarker of Alzheimer disease comprising the peptides selected from the group consisting of amino acid sequence expressed by SEQ ID NO: 4 that is disappeared or decreased in biological material of patients of Alzheimer disease as compared to biological material of subjects not suffering from non-demented neurological disease.

[8] Method for detection of psychiatric disease involving determination in biological material of at least one biomarker for psychiatric disease as described in [1] or [2].

[9] Method for detection of cognitive impairment involving determination in biological material of at least one biomarker for cognitive impairment as described in [1] or [3].

[10] Method for detection of cognitive impairment in which patient is judged as suffering from cognitive impairment when, after determination in biological material of at least one biomarker for cognitive impairment as described in [4], said biomarker is found to be present in higher quantity than in subjects not suffering from psychiatric disease.

[11] Method for detection of cognitive impairment in which patient is judged as suffering from cognitive impairment when, after determination in biological material of at least one biomarker for cognitive impairment as described in [5], said biomarker is found to be present in lower quantity than in subjects not suffering from psychiatric disease.

[12] Method for detection of psychiatric disease as described in [8] wherein detection is made either by immunoblot procedure, Western blotting, enzyme-, fluorescence-, or radioisotope-labeled antibody method, mass spectrometry, immunoMS method or surface plasmon resonance method.

[13] Method for detection of cognitive impairment as described in any of [9] to [11] wherein detection is made either by immunoblot procedure, Western blotting, enzyme-, fluorescence-, or radioisotope-labeled antibody method, mass spectrometry, immunoMS method or surface plasmon resonance method.

[14] A kit for detection of psychiatric disease to determine at least one biomarker as described in [1] or [2].

[15] A kit for detection of cognitive impairment to determine at least one biomarker as described in any of claims [1], [3] to [5].

[16] A kit for detection of psychiatric disease containing antibody or aptamer to at least one biomarker as described in [1] or [2].

[17] A kit for detection of psychiatric disease containing antibody or aptamer to at least one biomarker as described in any of claims [1], [3] to [5].

[18] A kit for detection as described in [16] or [17] wherein antibody or aptamer is solidified on a plate or plates.

Advantageous Effects of Invention

According to the present invention, it is possible to diagnose a subject as to whether said subject has suffered from psychiatric disease or cognitive impairment by determining in biological material obtained from said subject the kind and amount of at least one peptide selected from the group consisting of Neurexin-2-beta precursor-derived peptide NRX2B consisting of amino acid sequence expressed by SEQ ID NO: 2, Prothrombin precursor-derived peptide THRB(R−) consisting of amino acid sequence expressed by SEQ ID NO: 4, Prothrombin precursor-derived peptide THRB(R+) consisting of amino acid sequence expressed by SEQ ID NO: 5, Pendrin-derived peptide S26A4 consisting of amino acid sequence expressed by SEQ ID NO: 7, Coatomer subunit zeta-1-derived peptide COPZ1 consisting of amino acid sequence expressed by SEQ ID NO: 9, Retinoic acid receptor responder protein 2 precursor-derived peptide RARR2(S−) consisting of amino acid sequence expressed by SEQ ID NO: 11, Retinoic acid receptor responder protein 2 precursor-derived peptide RARR2(S+) consisting of amino acid sequence expressed by SEQ ID NO: 12, Gelsolin precursor-derived peptide GELS consisting of amino acid sequence expressed by SEQ ID NO: 14, Clusterin precursor-derived peptide CLUS(N-term SDVP) consisting of amino acid sequence expressed by SEQ ID NO: 16, Clusterin precursor-derived peptide CLUS(N-term RFFT) consisting of amino acid sequence expressed by SEQ ID NO: 17, Eukaryotic translation initiation factor 3 subunit J-derived peptide EIF3J consisting of amino acid sequence expressed by SEQ ID NO: 19, and Leucine-rich repeat-containing protein 27-derived peptide LRC27 consisting of amino acid sequence expressed by SEQ ID NO: 21. In addition, it is possible to diagnose a subject has suffering from Alzheimer's disease when compared with the increase in biological material of patients of non-demented neurological disease by determining amount of peptide consisting of amino acid sequence expressed by SEQ ID NO: 2, and it is possible to diagnose a subject has suffering from Alzheimer's disease when compared with the decrease in biological material of patients of non-demented neurological disease by determining amount of peptide consisting of amino acid sequence expressed by SEQ ID NO: 4.

The present invention presents a diagnostic system that is high in both accuracy and specificity. The present invention enables highly accurate diagnosis of cognitive impairment in which there have been no specific test methods for such biological materials as blood. Furthermore, the biomarkers disclosed in the present invention are highly useful in judgment of drug efficacy.

BRIEF DESCRIPTION OF DRAWINGS

FIG. 2A) illustrates the comparison between ADN, MCI and AD, and FIG. 2B) illustrates the comparison between ADN, AD, NDall, NDdem and NDnon. For each samples, the average value (divided by 1,000) and (SD) (divided by 1,000) are as follows. FIG. 2A) ADN 0.1 (0.1); MCI 45.8 (42.2); AD 41.7 (22.2).

Abbreviations used are; AD (Alzheimer's disease), ADN (subjects not suffering from psychiatric disease and age and sex-matched patients with AD, "N" means normal), NDall (neurological disease), NDdem (demented neurological disease), NDnon (non-demented neurological disease).

Figure 3:
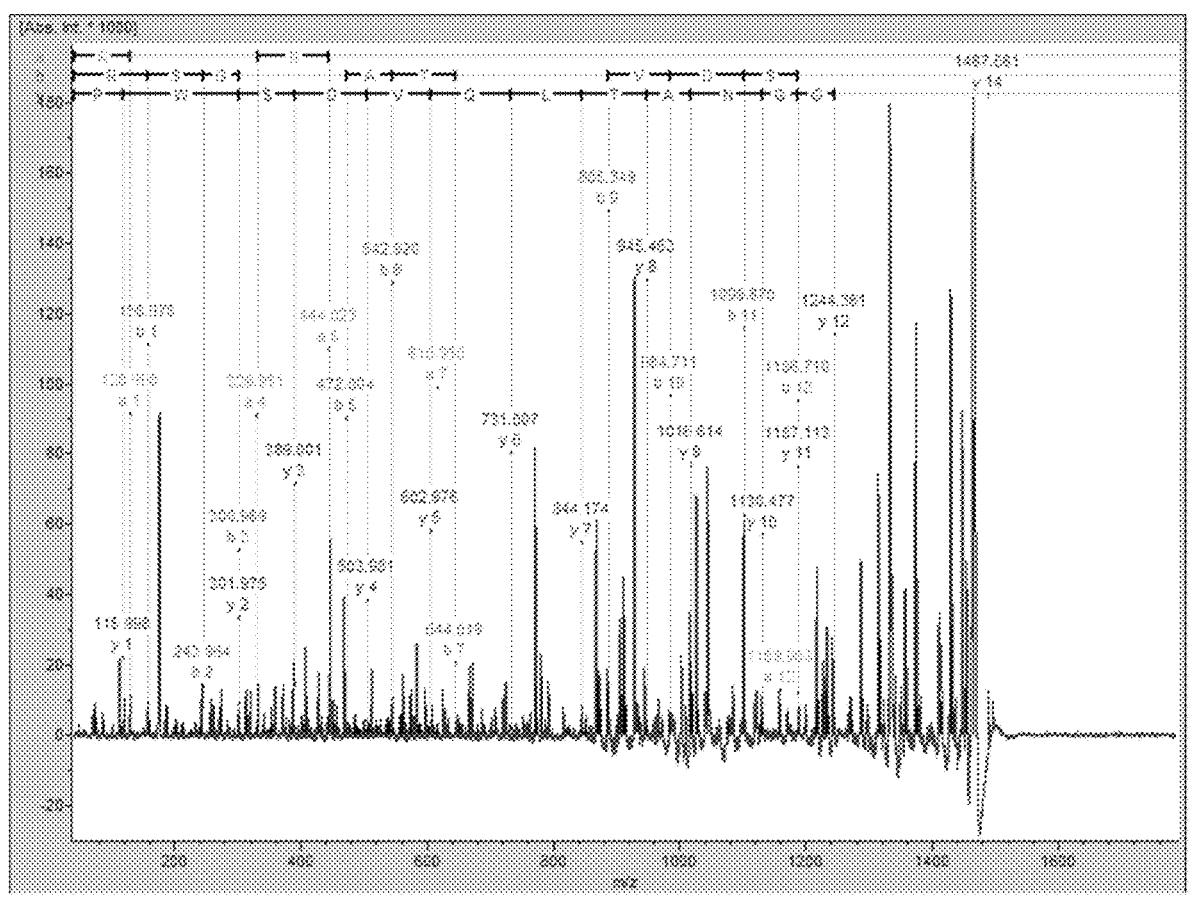
As shown in FIG. 3, Marker A is Neurexin-2-beta precursor-derived peptides NRX2B.

FIG. 3 illustrates the MS/MS spectrum of Marker A (SEQ ID NO: 2, NRX2B) obtained by using TOF/TOF mass spectrometer. (Example 1)

FIGS. 4A)-4D) illustrate the comparison between non-psychiatric disease subjects (ADN) and patients of psychiatric disease including sementia for THRB(R−) FIGS. 4A) and 4B), and THRB(R+) FIGS. 4C) and 4D) in serum. (Example 1)

FIG. 5A) illustrates the each individual comparison between non-psychiatric disease subjects (ADN) and patients of cognitive impairment (MCI, AD) patient for THRB(R−) and THRB(R+) in serum. FIG. 5B) illustrates the ROC curve of the comparison of AD vs. NDdon for THRB(R−) in serum. (Example 1)

Figure 6A:
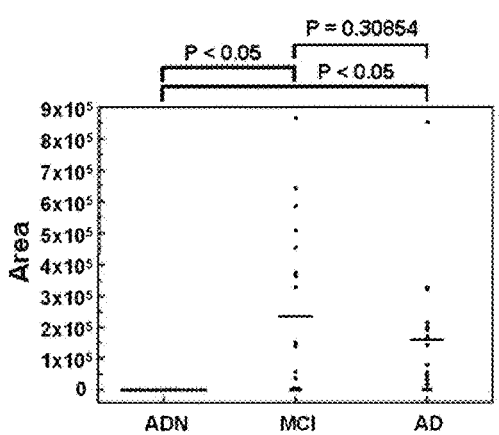
Figure 6B:
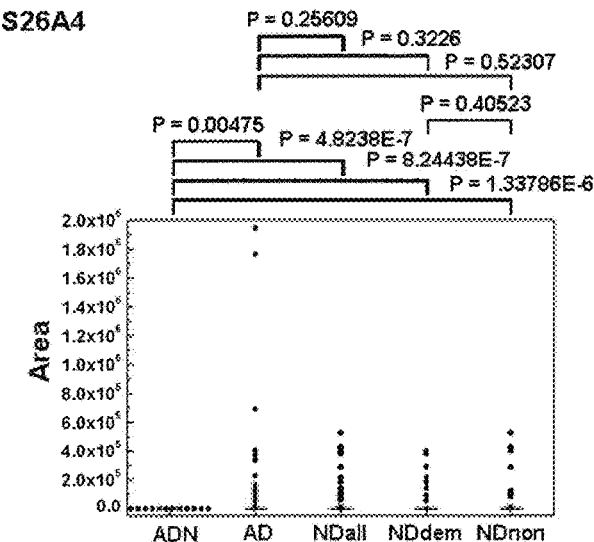
Figure 6C:
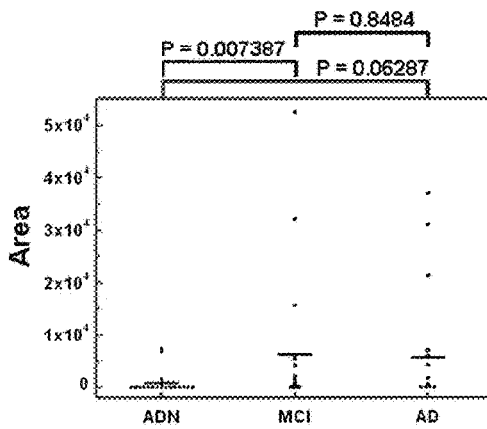
Figure 6D:
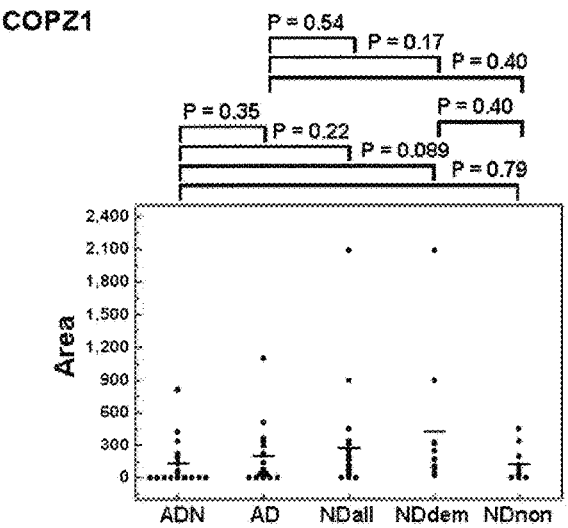

FIGS. 6A) and 6B) illustrate the comparison between non-psychiatric disease subjects (ADN) and patients of psychiatric disease including dementia for S264A in serum, and FIGS. 6C) and 6D) illustrate the comparison between non-psychiatric disease subjects (ADN) and patients of psychiatric disease including dementia for COPZ1 in serum. (Example 1)

Figure 7A:
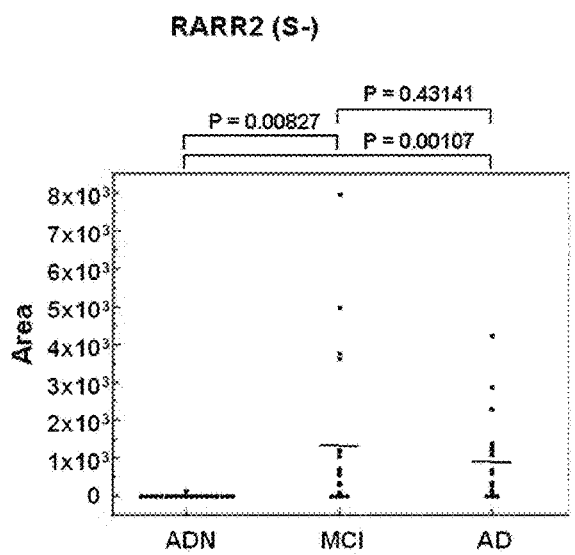

FIGS. 7A) and 7B) illustrate each individual comparison between non-psychiatric disease subjects (ADN) and patients of cognitive impairment (MCI, AD) patient for PARR2(S−) and PARR2(S+) 7B)) in serum. (Example 1)

Figure 8A:
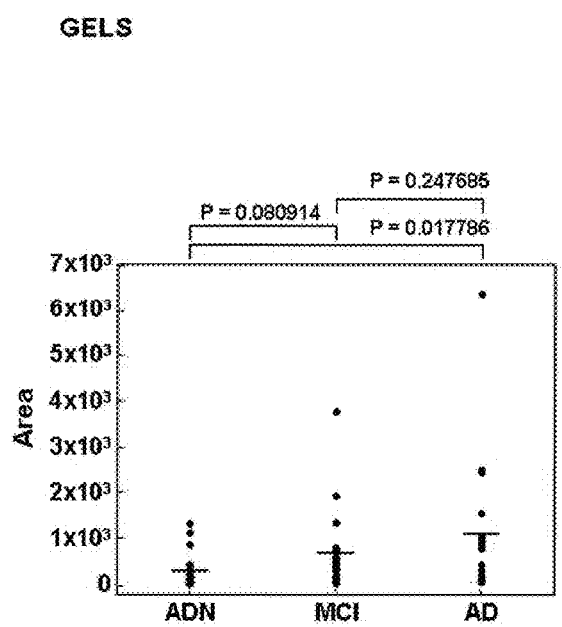
Figure 9A:
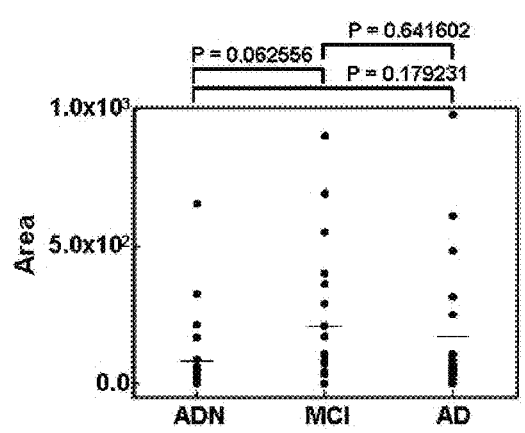
Figure 9B:
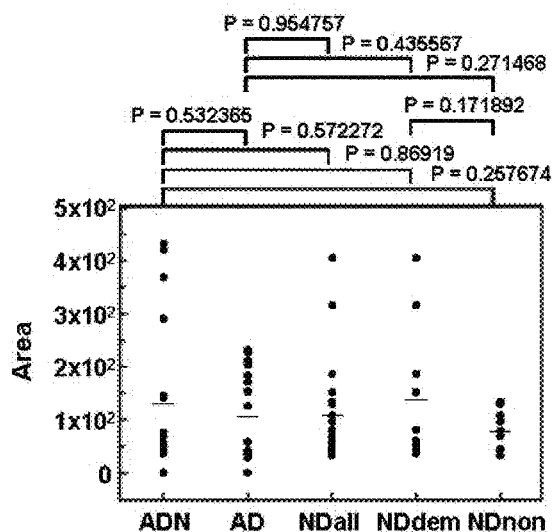
Figure 9C:
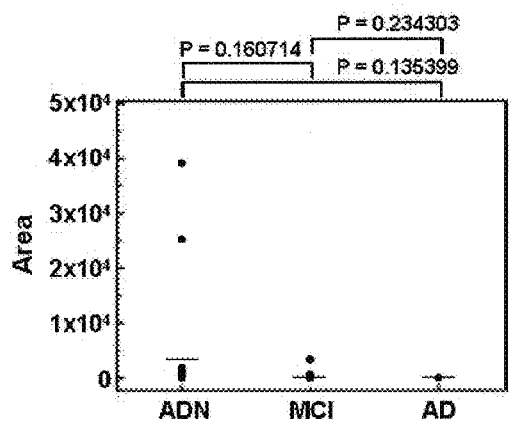
Figure 9D:
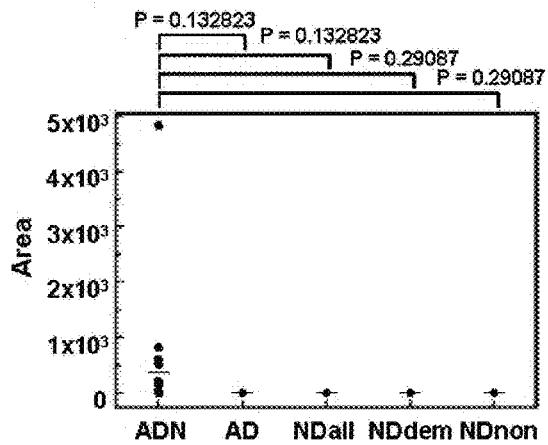

FIGS. 8A) and 8B) illustrate the comparison between non-psychiatric disease subjects (ADN) and patients of psychiatric disease including dementia for GELS in serum. (Example 1) FIGS. 9A) and 9B) illustrate the comparison between non-psychiatric disease subjects (ADN) and patients of psychiatric disease including dementia for CLUS (N-term SDVP) in serum, and FIGS. 9C) and 9D) illustrate the comparison between non-psychiatric disease subjects (ADN) and patients of psychiatric disease including dementia for CLUS(N-term RFFT) in serum. (Example 1)

FIGS. 10A) and 10B) illustrate the comparison between non-psychiatric disease subjects (ADN) and patients of psychiatric disease including dementia for EIF3J in serum, and FIG. 10C) illustrates the comparison between non-psychiatric disease subjects (ADN) and patients of cognitive impairment (MCI, AD) patient for LRC27 in serum. (Example 1)

FIGS. 11A) and 11B) illustrate the mass spectrum of NRX2B peptide that captured and detected by immunoMS method using NRX2B-specific antibody from the serum of AD and MCI patients. FIG. 11A) is the enlarged view of arrow parts in FIG. 11B). Endogenous NRX2B peptide (solid arrows) and stable isotope labeled-NRX2B synthetic peptide NRX2B (dashed arrows) are shown for each peak FIG. 11A). (Example 4)

DESCRIPTION OF EMBODIMENTS

The present invention is a method for determining the kind and the amount of intact protein and/or its partial peptide when test subject is suffering from cognitive impairment as well as for diagnosing whether test subject is suffering from cognitive impairment and, whether test subject is diagnosed to be suffering from psychiatric disease. A peptide is generally said to be a chemical entity, made by polymerizing a number of amino acids, of less than 10,000 in molecular weight or by polymerizing several to less than about 50 amino acid residues. While in the present invention a partial peptide of an intact protein can be used as a biomarker for detection of cognitive impairment, such partial peptide is defined as a peptide of less than 10,000 in molecular weight consisting of a part of the amino acid sequence of the intact protein. Such peptide may arise as a partial peptide during the expression by transcription followed by synthesis by translation before maturing into an intact protein or as a peptide produced by enzyme digestion in the body after the intact protein has been synthesized. It is possible that, when the body is in abnormal state suffering from such disease as cognitive impairment, the mechanism for protein synthesis and regulation is de-regulated. In other words, the present invention is also a method for determining if test subject is in normal state or is suffering from cognitive impairment by using the degree of protein synthesis and/or protein digestion as an indicator. The detection of cognitive impairment in the present invention means evaluation and differentiation, i.e., diagnosis of test subject as to whether the subject is suffering from cognitive impairment. The present invention can also include the evaluation of patient's risk of suffering from more serious cognitive impairment.

Specifically, in the method of the present invention, the examples of intact protein that can be used as a cognitive impairment include Neurexin-2-beta precursor consisting of amino acid sequence expressed by SEQ ID NO: 1, Pro-thrombin precursor consisting of amino acid sequence expressed by SEQ ID NO: 3, Pendrin consisting of amino acid sequence expressed by SEQ ID NO: 6, Coatomer subunit zeta-1 consisting of amino acid sequence expressed by SEQ ID NO: 8, Retinoic acid receptor responder protein 2 precursor consisting of amino acid sequence expressed by SEQ ID NO: 10, Gelsolin precursor consisting of amino acid sequence expressed by SEQ ID NO: 13, Clusterin precursor consisting of amino acid sequence expressed by SEQ ID NO: 15, Eukaryotic translation initiation factor 3 subunit J consisting of amino acid sequence expressed by SEQ ID NO: 18, and Leucine-rich repeat-containing protein 27 consisting of amino acid sequence expressed by SEQ ID NO: 20, and further, the peptide fragments that comprise of partial peptides of not less than 5 amino acid residues of these intact proteins can be used as same purpose.

Still further, an example of biomarkers for cognitive impairment of the present invention includes the partial peptides consisting of amino acid sequence expressed by SEQ ID NO: 2 of Neurexin-2-beta precursor-derived peptide NRX2B, SEQ ID NO: 4 of Prothrombin precursor-derived peptide THRB(R−), SEQ ID NO: 5 of Prothrombin precursor-derived peptide THRB(R+), SEQ ID NO: 7 of Pendrin-derived peptide S26A4, SEQ ID NO: 9 of Coatomer subunit zeta-1-derived peptide COPZ1, SEQ ID NO: 11 of Retinoic acid receptor responder protein 2 precursor-derived peptide RARR2(S−), SEQ ID NO: 12 of Retinoic acid receptor responder protein 2 precursor-derived peptide RARR2(S+), SEQ ID NO: 14 of Gelsolin precursor-derived peptide GELS, SEQ ID NO: 16 of Clusterin precursor-derived peptide CLUS(N-term SDVP), SEQ ID NO: 17 of Clusterin precursor-derived peptide CLUS(N-term RFFT), SEQ ID NO: 19 of Eukaryotic translation initiation factor 3 subunit J-derived peptide EIF3J, SEQ ID NO: 21 of Leucine-rich repeat-containing protein 27-derived peptide LRC27. In the present invention, proteins and peptides consisting of amino acid sequences derived from SEQ ID NO: 1 to 21 by deletion, exchange, and/or addition of one or a few amino acids can be used as biomarkers and are included in the present invention. '"One or a few" herein means "one or three," "one or two," or "one." Furthermore, the partial peptides that can be used as biomarkers in the present invention include those peptide fragments consisting of not less than 5 amino acid residues arising respectively from SEQ ID NO: 1 to 21. The basis for the limitation of peptide fragments consisting of not less than 5 amino acid residues is in the description below in Non-patent Document 2. The document reported that an antibody obtained by using the peptide IRGERA (SEQ ID NO: 23) as immunogen, which was the C-terminus (130-135) of histone H3, recognized the peptide IKGERA (SEQ ID NO: 24) derived by exchange of K for R and the peptide CGGGERA (SEQ ID NO: 25) which was derived by deletion of IR followed by addition of CGG. This demonstrates that the immunogenicity (antigenicity) is recognized by a peptide of not less than 4 amino acid residues. In order to expand this finding to other peptides than the C-terminus of histone H3, the number of amino acid residue is defined as not less than 5 instead of 4 in the present invention. To make such a low molecular weight peptide as the subject of the present invention is important when the method of detection and differentiation uses immunological means including immunoblot, ELISA and immunoMS.

It is to be noted that there are cases where a sugar chain or sugar chains have been added to an intact protein or its partial peptide to form glycated entities. Proteins and partial peptides in glycated form can also be used as biomarkers for detection of cognitive impairment.

It is also to be noted that, in the present invention, biomarker can be quantified or its presence or absence can be determined qualitatively.

Two-dimensional electrophoresis (2-DE) or 2-dimensional chromatography (2-DC) can be used in the present invention to separate biomarkers in biological materials including serum. Known chromatographic methods can be selected from ion-exchange chromatography, reverse-phase chromatography and gel-filtration chromatography. It is also possible to make quantification with the SRM/MRM method in LC-MS/MS technology. Furthermore, the immunoMS method which these inventors have developed, where target protein or peptide is captured by beads (including magnetic ones) with antibody linked to the protein or peptide, eluted from the beads, and determined by mass spectrometry enables convenient determination of presence or absence or the amount of target protein, protein fragment or peptide without the use of 2-DE or chromatography.

It is possible with the method disclosed in the present invention to evaluate at the stage of mild of cognitive dysfunction in test subject and therefore it can be useful in prophylactic medicine. Further, when psychotherapy and/or drug therapy is given to patients with cognitive impairment, it is reflected in the amount of proteins and partial peptides in biological materials such as serum if the progression of the disorder has been inhibited. Therefore, by measuring these proteins and partial peptides, it is possible to evaluate and determine therapeutic effect.

The kind and amount of a protein in biological materials can be determined by various methods. If target protein (including protein fragment and partial peptide) has been characterized and when an antibody (primary antibody) to it has already been obtained, the following methods can be used:

1. Immunoblot

This is one of the simplest methods. Test serum in a fixed amount (about 1 microliter) after stepwise dilution is dropped onto an appropriate membrane such as of nitrocellulose and dried in air. The membrane is treated with a blocking solution containing a protein such as BSA, washed, reacted with primary antibody, and washed. Thereafter, the membrane is reacted with labeled secondary antibody to detect the primary antibody. The membrane is washed and the label is visualized to measure its density.

2. Western Blotting

After separation with one-dimensional or two-dimensional electrophoresis involving isoelectric focusing or SDS-PAGE, proteins are transferred onto such an appropriate membrane as of nitrocellulose and their amounts are determined, as in above-mentioned immunoblot, using primary antibody and labeled secondary antibody.

3. ELISA

Antibody to protein or its partial peptide is fixed to such a plate as a chemically modified microtiter plate. Appropriate amounts of samples after stepwise dilution are applied to the plate and incubated. Proteins and peptides not captured are removed by washing. Next, the plate is incubated with secondary antibody labeled with fluorescent or chemiluminescent substance or enzyme. After addition of respective substrate, fluorescence, chemiluminescence or visible light due to enzyme reaction is measured for evaluation and judgment.

Additional examples of methods are illustrated below (see PTL 2) but the invention is not limited by these examples.

4. Methods that Use Microarray (Microchip)

A microarray is a general term for devices where solidified materials with affinity for target substances are arrayed on solid support (plate). In the present invention, antibodies or aptamers to proteins and partial peptides are arrayed. A sample of biological material is placed on the microarray for fixation of target proteins or partial peptides and the microarray is then incubated with secondary antibody labeled with fluorescent or chemiluminescent substance or enzyme. After addition of respective substrate, fluorescence, chemiluminescence or visible light due to enzyme reaction is measured.

5. Mass Spectrometry

In mass spectrometry, for example, antibody to a specified protein or partial peptide is attached to chemically modified microbeads or plate (protein chip). The microbeads could be magnetic beads. There are no requirements for the material of the plate. The antibody to be used could be (1) an antibody which recognizes the full length form of the specified protein only, (2) an antibody which recognizes a partial peptide only, (3) all of antibodies which recognizes both the specified protein and its partial peptide, or a combination of (1) and (2), (1) and (3), or (2) and (3). Samples after stepwise dilution with original solvent or buffer are added to the microbeads or plate carrying antibody or antibodies and incubated. Those proteins and partial peptides not captured are removed by washing. The protein or partial peptide captured by microbeads or plate is eluted, and analyzed by mass spectrometry with MALDI-TOF-MS, SELDI-TOF-MS, etc. Measurements are made with respect to the mass and intensity of the peak due to the protein, protein fragment or partial peptide. Prior to the measurements a fixed amount of substance serving as the internal standard is added to the original biological material and the intensity of its peak is also measured. The concentration of the target in the original biological material can be calculated from the ratio of peak intensity of the target to the peak intensity of the internal standard. This is called immunoMS method. Further, it is possible to make quantification, after the sample is diluted with original solvent or buffer, or after part of proteins are removed, by separation with HPLC followed by mass spectrometry with electrospray ionization (ESI) method. Therein the SRM/MRM method can be utilized for absolute quantification with the use of an isotope-labeled internal standard peptide.

Furthermore, in addition to the above-mentioned methods, it is possible to analyze proteins and partial peptides by using 2-DE, surface plasmon resonance, etc.

The present invention includes the method to detect cognitive impairment from the presence or absence or amount of the above-mentioned biomarker after applying biological material obtained from test subject to 2-DE or surface plasmon resonance.

Example 1

Discovery of a marker peptide for detection of cognitive impairment using two-dimensional liquid chromatography (2D-LC)-MALDI TOF-MS.

(1) Serum Samples.

Followings, the characters before the parenthesis are an abbreviation.

A sera obtained from 20 AD (Alzheimer's disease), 20 ADN (subjects not suffering from psychiatric disease and age and sex-matched patients with AD, "N" means normal), and 20 NDall (neurological disease) were used. NDall consists of 10 NDdem (demented neurological disease) and 10 NDnon (non-demented neurological disease). Furthermore, NDdem consists of dementia with Lewy body and frontotemporal dementia each consisting of 5 cases, and NDnon consists of schizophrenia and depression each consisting of 5 cases.

(2) Methods

After 475 μl of 0.1% trifluoroacetic acid (TFA) were added in each of 25 μl of sera, samples were boiled for 15 min at 100 degrees. Subsequently, in order to recover peptides of molecular weight of 10,000 or less, ultrafiltration were performed by using YM-10 filter unit (Millipore Corp.). Then the analysis using 2D-LC-MALDI TOF-MS were performed as follows. In other words, recovering samples were fractionated to 1,146 fractions per sample by using two-dimensional HPLC (SCX cation exchange column and C18 reverse-phase column). All fractionated samples were spotted on MALDI target plate for MALDI TOF/TOF mass spectrometer (ultraflex TOF/TOF, Bruker Daltonics), and matrix solution (alpha-cyano-hydroxycinnamic acid, CHCA) were mixed and crystallized, and the mass and the peak area of the mass were measured automatically in refrectron mode by irradiating to crystallized sample by laser. Peak area was normalized with 250 fmole of per each well of bradykinin 1-7 fragment that was added into matrix solution in advance. In other words, the area value was calculated in 10,000 times of the value dividing the peak area in specific mass of sample by the peak area obtained from 250 fmole of bradykinin1-7 fragment. This area value is corresponding in 25 μl of sample serum. Detection of difference in abundance of peptides in serum between groups (called differential analysis) was performed using multi-group statistical analysis software DeView developed by us. Peptide that was observed to difference in abundance was directly determined amino acid sequence in MS/MS analysis by ultraflex TOF/TOF, and intact proteins or peptides of their origin were identified.

(3) Results

Figure 1:
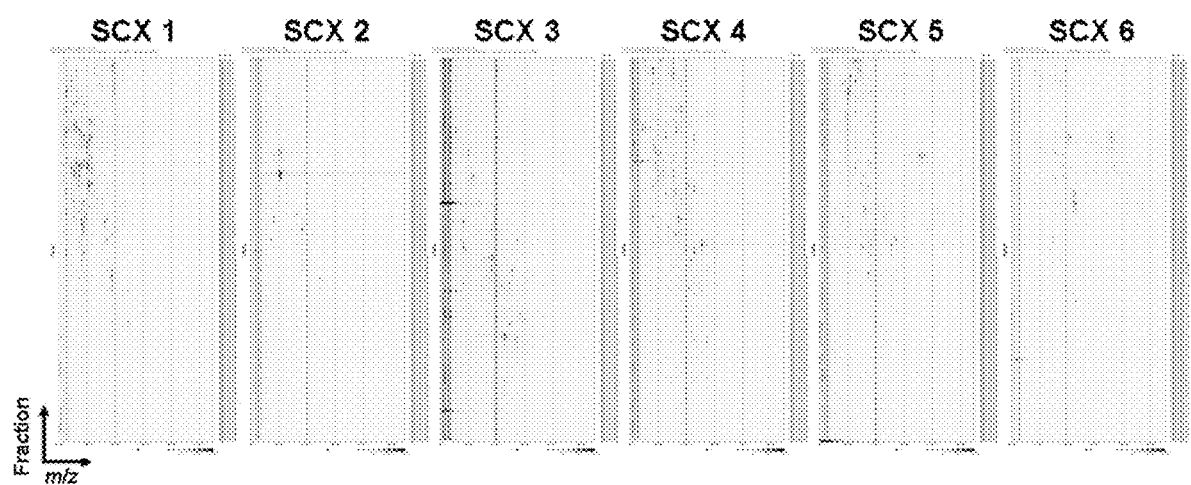
FIG. 1 illustrates the isolation of serum of Alzheimer's disease by 2D-LC-MALDI TOF-MS method. (Example 1)
Figure 2A:
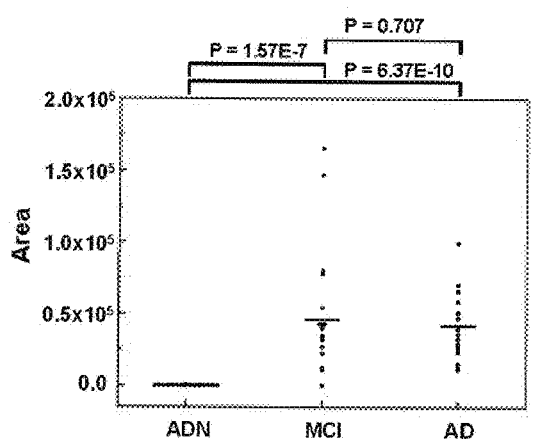
FIGS. 2A)-2E) illustrate the case of Marker A that is the one example of the result of differential analysis.
Figure 2B:
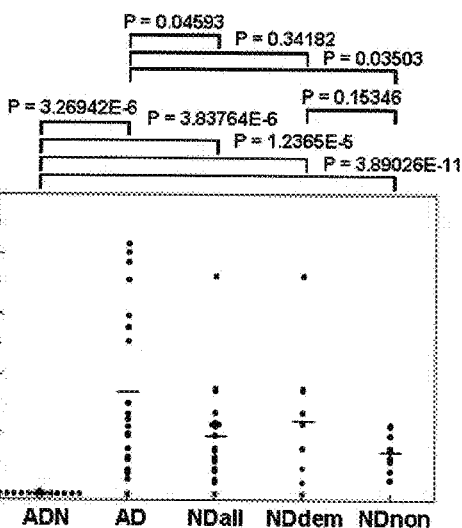
FIG. 2B) ADN 0.1 (0.2); AD 34.0 (27.8); NDall 19.2 (15.8); NDdem 24.3 (20.8); NDnon 14.0 (6.1).
Figure 2C:
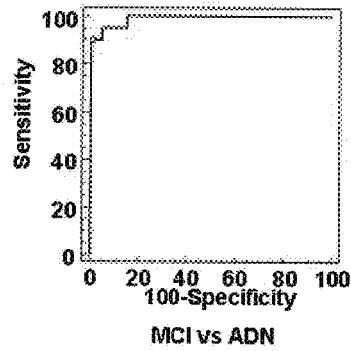
FIGS. 2C), 2D), and 2E), respectively, the ROC curve of the comparison of MCI vs. ADN, AD vs. ADN, and AD vs. NDnon. (Example 1)
Figure 2D:
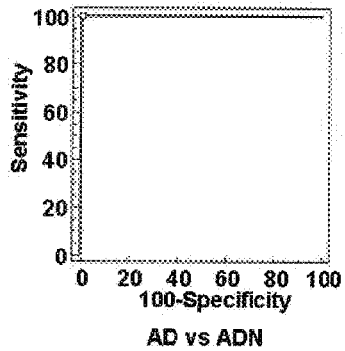
Figure 2E:
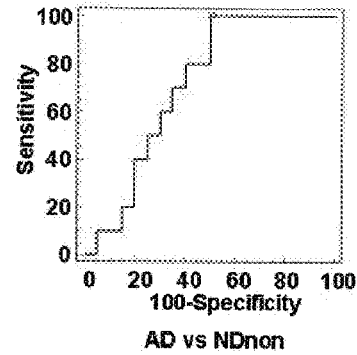

FIG. 1 shows the result that was obtained from serum of one case of AD patient that was applied to 2D-LC-MALDI TOF-MS. Sample was fractionated into 6 fractions by SCX cation exchange column in the first dimension, then each of fractions were fractionated into 191 fractions by C18 reverse-phase column. Mass spectra of 191 fractions were obtained by MALDI TOF-MS measuring. As the horizontal axis is the m/z and the vertical axis is the fractions of reverse-phase column chromatography, FIG. 1 was visualized by Deview software developed by present inventors. SCX 1 shows flow-through fractions, SCX 2 shows fractions eluted in 10% salt concentration, SCX 3 shows fractions eluted in 20% salt concentration, SCX 4 shows fractions eluted in 30% salt concentration, SCX 5 shows fractions eluted in 50% salt concentration, SCX 6 shows fractions eluted in 100% salt concentration. As seen in FIG. 1, many peptides in many sera are present in fractions of SCX1, SCX 3, SCX 4, and SCX 5. Total numbers of peptides fractionated by 2D-LC and detected by MALDI TOF-MS were about 4,000.

As one example of the results of differential analysis, FIG. 2 shows the case of Marker A. Marker A, as shown later in FIG. 3, is Neurexin-2-beta precursor-derived peptide NRX2B. A) of FIG. 2 shows a comparison between ADN, MCI, AD. A) and B) shows the result of experiments carried out separately, ADN and AD were used the same samples in both experiments (i.e., for ADN and AD, the measurement results would indicate the reproducibility). In A) of FIG. 2, it was found that Marker A is increased in MCI and AD patients than ADN patient. In B) of FIG. 2, it was found that Marker A is increased in AD, NDall, NDdem, and NDnon patients than ADN patient. In particular, in comparison of AD and NDnon, AD was significantly higher than NDnon (t-test, p=0.035). From these results, it was found that Marker A was useful to distinguish between cognitive impairment (MCI, AD, NDdem) patient and non-demented neurological disease (NDnon).

From the results of A) and B) in FIG. 2, in order to evaluate the extent to which the Marker A is useful as biomarker, the analysis by receiver operating characteristic (ROC) curve was performed. C), D) and E) in FIG. 2 shows respectively the ROC curve of the comparison of MCI vs. ADN, AD vs. ADN, and AD vs. NDnon. If the area value (hereinafter referred to as the ROC value) of under the ROC curve is close to 1, the usefulness as biomarker of Marker A will be higher. In C), D), E) of FIG. 2, the typical values of sensitivity and specificity are the values of the point (open square in the figure) of the coordinate on ROC curve that the distance is minimized when a straight line was drawn to ROC curve from the point of 100% on y-axis. The value of cut-off giving this point becomes a useful threshold to distinguish between the different groups, and the values of sensitivity and specificity at that time (i.e., above the typical values) becomes an indicator of the usefulness of biomarkers together with ROC values. In C) of FIG. 2, as typical values in MCI vs. ADN, the sensitivity was 90%, the specificity was 100%, and the ROC value was 0.99. In D) of FIG. 2, as typical values in AD vs. ADN, the sensitivity was 100%, the specificity was 100%, and the ROC value was 1. In E) of FIG. 2, it was comparing between AD vs. CCC, the sensitivity was 100%, the specificity was 50%, and the ROC value was 0.710. Thus, it was revealed that Marker A (NRX2B) was useful to distinguish MCI and AD with ADN. And also, it was revealed that Marker A was useful to distinguish AD with non-demented neurological disease (NDnon). In particular, since MCI is the state of previous stage of AD, Marker A (NRX2B) is considered to be a extremely useful marker to detect MCI for early diagnosis of potential subjects to migrate to AD.

FIG. 3, for Marker A, illustrates the results of MS/MS spectrum using ultraflex TOF/TOF. The signals that show y-ions and b-ions have enough appeared, and the amino acid sequence could be readily identified. Mascot search was performed on this result, and the protein of origin or the peptide (hereinafter referred to as intact proteins or peptides)

is Neurexin-2-beta precursor, and the detected peptide was found that the sequence is RSGGNATLQVDSWP (SEQ ID NO: 2). NRX2B of entry name of Swiss-Prot against Neurexin-2-beta precursor will use as an abbreviation of the peptide name. Also as for other peptides that were detected, the entry names of Swiss-Prot will be used as abbreviations of the peptide names in the following descriptions.

Including the Marker A, the peptides that have difference in abundance between the groups in serum were measured MS/MS spectra using ultraflex TOF/TOF, and in addition to determining the amino acid sequence, the results identified intact proteins or peptides were shown below. For peptides other than Marker A, the signals that show y-ions and b-ions has enough appeared, and the amino acid sequence could be readily identified. The following amino acid sequence that shows a set of two sequences, the entire sequence of the first sequence shows the amino acid sequence of intact proteins or peptides. The peptide comprising of the underlined portion of the first sequence and the second sequence is peptide detected by 2D-LC-MALDI TOF-MS. 001 represents N-terminus. The peptide which has oxidation of methionine was indicated as (+Oxidation (M)) at the end of the amino acid sequence. For the protein with mutation of amino acid by gene mutation, applicable amino acid residue was expressed with (X).

(1) Neurexin-2-beta Precursor-Derived Peptide NRX2B

NRX2B shown as SEQ ID NO: 2 was not detected in ADN patient, and was detected in MCI, AD, NDall, NDdem, and NDnon patients. Furthermore, in comparison of AD and NDnon, AD shown higher value than NDnon, NRX2B was shown distinction ability (previously described in FIG. 2).

Intact protein/peptide

```
                                         (SEQ ID NO: 1)
001 MPPGGSGPGG CPRRPPALAG PLPPPPPPPP PPLLPLLPLL
    LLLLLGAAEG

051 ARVSSSLSTT HHVHHFHSKH GTVPIAINRM PFLTRGGHAG
    TTYIFGKGGA

101 LITYTWPPND RPSTRMDRLA VGFSTHQRSA VLVRVDSASG
    LGDYLQLHID

151 QGTVGVIFNV GTDDITIDEP NAIVSDGKYH VVRFTRSGGN
    ATLQVDSWPV

201 NERYPAGNFD NERLAIARQR IPYRLGRVVD EWLLDKGRQL
    TIFNSQAAIK

251 IGGRDQGRPF QGQVSGLYYN GLKVLALAAE SDPNVRTEGH
    LRLVGEGPSV

301 LVASAECPSD DEDLEECEPS TGGELILPII TEDSLDPPPV
    ATRSPFVPPP

351 PTFYPFLTGV GATQDTLPPP AARRPPSGGP CQAERDDSDC
    EEPIEASGFA

401 SGEVFDSSLP PTDDEDFYTT FPLVTDRTTL LSPRKPAPRP
    NLRTDGATGA

451 PGVLFAPSAP APNLPAGKMN HRDPLQPLLE NPPLGPGAPT
    SFEPRRPPPL

501 RPGVTSAPGF PHLPTANPTG PGERGPPGAV EVIRESSSTT
    GMVVGIVAAA

551 ALCILILLYA MYKYRNRDEG SYQVDQSRNY ISNSAQSNGA
    VVKEKAPAAP

601 KTPSKAKKNK DKEYYV
```

Neurexin-2-beta Precursor-Derived Peptide NRX2B

```
                                         (SEQ ID NO: 2)
RSGGNATLQVDSWP
```

(2) Prothrombin Precursor-Derived Peptide (THRB(R−))

Prothrombin precursor-derived peptides are two types, and (R−) means the peptide lacking of R (Arginine residue) of C-terminus. THRB(R−) shown as SEQ ID NO: 4 was detected specifically in ADN patient, and was detected extremely low value in MCI, AD, NDall, NDdem, NDnon patients. Diagrams of THRB(R−) and THRB(R+) showed side by side in FIG. 4 and FIG. 5. FIG. 4 shows scatter plot. FIG. 5A) shows that the appearance of THRB(R−) and THRB(R+) how is different in every individual of ADN, MCI and AD. In the same individual, THRB(R−) has appeared overwhelmingly in ADN, THRB(R+) has appeared overwhelmingly in MCI and AD. It can be said that both peptides are extremely useful markers determining MCI and ADN. FIG. 5B) shows ROC curve comparing AD and NDnon of THRB(R−). ROC value indicated a high value of 0.815. the value in AD was lower compared to NDnon. In other words, it has been found that THRB(R−) as well as NRX2B is useful marker to distinguish between patients of cognitive impairment (MCI, AD, NDdem) and patients of non-demented neurological disease (NDnon).

Intact protein/peptide

```
                                         (SEQ ID NO: 3)
001 MAHVRGLQLP GCLALAALCS LVHSQHVFLA PQQARSLLQR
    VRRANTFLEE

051 VRKGNLEREC VEETCSYEEA FEALESSTAT DVFWAKYTAC
    ETARTPRDKL

101 AACLEGNCAE GLGTNYRGHV NITRSGIECQ LWRSRYPHKP
    EINSTTHPGA

151 DLQENFCRNP DSSTTGPWCY TTDPTVRRQE CSIPVCGQDQ
    VTVAMTPRSE

201 GSSVNLSPPL EQCVPDRGQQ YQGRLAVTTH GLPCLAWASA
    QAKALSKHQD

251 FNSAVQLVEN FCRNPDGDEE GVWCYVAGKP GDFGYCDLNY
    CEEAVEEETG

301 DGLDEDSDRA IEGRTATSEY QTFFNPRTFG SGEADCGLRP
    LFEKKSLEDK

351 TERELLESYI DGRIVEGSDA EIGMSPWQVM LFRKSPQELL
    CGASLISDRW

401 VLTAAHCLLY PPWDKNFTEN DLLVRIGKHS RTRYERNIEK
    ISMLEKIYIH

451 PRYNWRENLD RDIALMKLKK PVAFSDYIHP VCLPDRETAA
    SLLQAGYKGR

501 VTGWGNLKET WTANVGKGQP SVLQVVNLPI VERPVCKDST
    RIRITDNMFC

551 AGYKPDEGKR GDACEGDSGG PFVMKSPFNN RWYQMGIVSW
    GEGCDRDGKY

601 GFYTHVFRLK KWIQKVIDQF GE
```

Prothrombin Precursor-Derived Peptide THRB(R−)

```
                                             (SEQ ID NO: 4)
GLDEDSDRAIEG
```

(3) Prothrombin Precursor-Derived Peptide (THRB(R+))

THRB(R+) shows as SEQ ID NO: 5 was not detected in ADN patient, and was detected in MCI, AD, NDall, NDdem, and NDnon patients (FIG. 4). (R+) means that the peptide having of R (Arginine residue) of C-terminus. For explanation, refer to (2) Prothrombin precursor-derived peptide (THRB(R−)).

```
Intact protein/peptide
                                             (SEQ ID NO: 3)
001 MAHVRGLQLP GCLALAALCS LVHSQHVFLA PQQARSLLQR
    VRRANTFLEE

051 VRKGNLEREC VEETCSYEEA FEALESSTAT DVFWAKYTAC
    ETARTPRDKL

101 AACLEGNCAE GLGTNYRGHV NITRSGIECQ LWRSRYPHKP
    EINSTTHPGA

151 DLQENFCRNP DSSTTGPWCY TTDPTVRRQE CSIPVCGQDQ
    VTVAMTPRSE

201 GSSVNLSPPL EQCVPDRGQQ YQGRLAVTTH GLPCLAWASA
    QAKALSKHQD

251 FNSAVQLVEN FCRNPDGDEE GVWCYVAGKP GDFGYCDLNY
    CEEAVEEETG

301 DGLDEDSDRA IEGRTATSEY QTFFNPRTFG SGEADCGLRP
    LFEKKSLEDK

351 TERELLESYI DGRIVEGSDA EIGMSPWQVM LFRKSPQELL
    CGASLISDRW

401 VLTAAHCLLY PPWDKNFTEN DLLVRIGKHS RTRYERNIEK
    ISMLEKIYIH

451 PRYNWRENLD RDIALMKLKK PVAFSDYIHP VCLPDRETAA
    SLLQAGYKGR

501 VTGWGNLKET WTANVGKGQP SVLQVVNLPI VERPVCKDST
    RIRITDNMFC

551 AGYKPDEGKR GDACEGDSGG PFVMKSPFNN RWYQMGIVSW
    GEGCDRDGKY

601 GFYTHVFRLK KWIQKVIDQF GE
```

Prothrombin Precursor-Derived Peptide THRB(R+)

```
                                             (SEQ ID NO: 5)
GLDEDSDRAIEGR
```

(4) Pendrin-Derived Peptide (S26A4)

S26A4 shows as SEQ ID NO: 7 was not detected in ADN patient, and was detected in MCI, AD, NDall, NDdem, and NDnon patients (FIG. 6).

```
Intact protein/peptide
                                             (SEQ ID NO: 6)
001 MAAPGGRSEP PQLPEYSCSY MVSRPVYSEL AFQQQHERRL
    QERKTLRES

051 AKCCSCSRKR AFGVLKTLVP ILEWLPKYRV KEWLLSDVIS
    GVSTGLVATL

101 QGMAYALLAA VPVGYGLYSA FFPILTYFIF GTSRHISVGP
    FPVVSLMVGS

151 VVLSMAPDEH FLVSSSNGTV LNTTMIDTAA RDTARVLIAS
    ALTLLVGIIQ

201 LIFGGLQIGF IVRYLADPLV GGFTTAAAFQ VLVSQLKIVL
    NVSTKNYNGV

251 LSIIYTLVEI FQNIGDTNLA DFTAGLLTIV VCMAVKELND
    RFRHKIPVPI

301 PIEVIVTIIA TAISYGANLE KNYNAGIVKS IPRGFLPPEL
    PPVSLFSEML

351 AASFSIAVVA YAIAVSVGKV YATKYDYTID GNQEFIAFGI
    SNIFSGFFSC

401 FVATTALSRT AVQESTGGKT QVAGIISAAI VMIAILALGK
    LLEPLQKSVL

451 AAVVIANLKG MFMQLCDIPR LWRQNKIDAV IWVFTCIVSI
    ILGLDLGLLA

501 GLIFGLLTVV LRVQFPSWNG LGSIPSTDIY KSTKNYKNIE
    EPQGVKILR

551 SSPIFYGNVD GFKKCIKSTV GFDAIRVYNK RLKALRKIQK
    LIKSGQLRAT

601 KNGIISDAVS TNNAFEPDED IEDLEELDIP TKEIEIQVDW
    NSELPVKVNV

651 PKVPIHSLVL DCGAISFLDV VGVRSLRVIV KEFQRIDVNV
    YFASLQDYV

701 EKLEQCGFFD DNIRKDTFFL TVHDAILYLQ NQVKSQEGQG
    SILETITLIQ

751 DCKDTLELIE TELTEEELDV QDEAMRTLAS
```

Pendrin-Derived Peptide S26A4

```
                                             (SEQ ID NO: 7)
LAGLIFGLLTVVLR
```

(5) Coatomer Subunit Zeta-1-Derived Peptide (COPZ1)

COPZ1 shows as SEQ ID NO: 9 was shown low value in ADN patient, was shown high value in MCI, AD, and NDdem patients (FIG. 6).

```
Intact protein/peptide
                                             (SEQ ID NO: 8)
001 MEALILEPSL YTVKAILILD NDGDRLFAKY YDDTYPSVKE
    QKAFEKNIFN

051 KTHRTDSEIA LLEGLTVVYK SSIDLYFYVI GSSYENELML
    MAVLNCLFDS

101 LSQMLRKNVE KRALLENMEG LFLAVDEIVD GGVILESDPQ
    QVVHRVALRG

151 EDVPLTEQTV SQVLQSAKEQ IKWSLLR
```

Coatomer Subunit Zeta-1-Derived Peptide COPZ1

```
                                             (SEQ ID NO: 9)
AILILDNDGDRLFAKYYDD
```

(6) Retinoic Acid Receptor Responder Protein 2 Precursor-Derived Peptide (RARR2(S−))

Figure 7B:
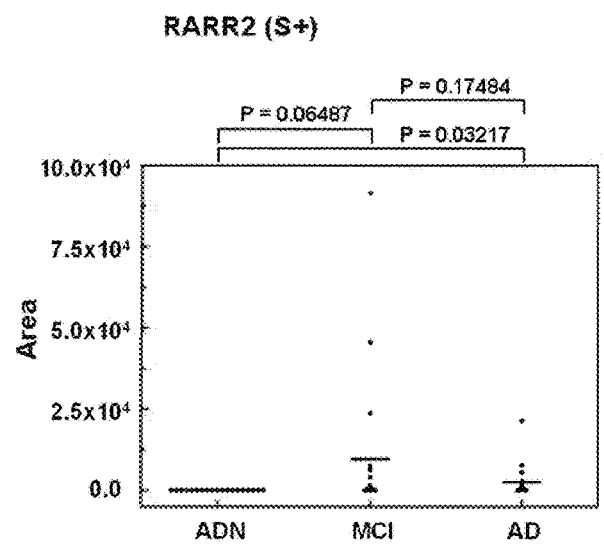

RARR2(S−) shows as SEQ ID NO: 11 was not detected in ADN patient, and was detected in AD and MCI patients (FIG. 7). Retinoic acid receptor responder protein 2 precursor-derived peptides are two types, and (S−) means the peptide lacking of S (Serine residue) of C-terminus.

```
Intact protein/peptide
                                               (SEQ ID NO: 10)
001 MRRLLIPLAL WLGAVGVGVA ELTEAQRRGL QVALEEFHKH
    PPVQWAFQET

051 SVESAVDTPF PAGIFVRLEF KLQQTSCRKR DWKKPECKVR
    PNGRKRKCLA

101 CIKLGSEDKV LGRLVHCPIE TQVLREAEEH QETQCLRVQR
    AGEDPHSFYF

151 PGQFAFSKAL PRS
```

Retinoic Acid Receptor Responder Protein 2 Precursor-Derived Peptide RARR2(S−)

```
                                               (SEQ ID NO: 11)
PHSFYFPGQFAFSKALPR
```

(7) Retinoic Acid Receptor Responder Protein 2 Precursor-Derived Peptide (RARR2(S+))

RARR2(S+) shows as SEQ ID NO: 12 was not detected in ADN patient as well as RARR2(S−), and was detected in AD and MCI patients (FIG. 7). (S+) means that the peptide having of S (Serine residue) of C-terminus.

```
Intact protein/peptide
                                               (SEQ ID NO: 10)
001 MRRLLIPLAL WLGAVGVGVA ELTEAQRRGL QVALEEFHKH
    PPVQWAFQET

051 SVESAVDTPF PAGIFVRLEF KLQQTSCRKR DWKKPECKVR
    PNGRKRKCLA

101 CIKLGSEDKV LGRLVHCPIE TQVLREAEEH QETQCLRVQR
    AGEDPHSFYF

151 PGQFAFSKAL PRS
```

Retinoic Acid Receptor Responder Protein 2 Precursor-Derived Peptide RARR2(S+)

```
                                               (SEQ ID NO: 12)
PHSFYFPGQFAFSKALPRS
```

(8) Gelsolin Precursor-Derived Peptide (GELS)

Figure 8B:
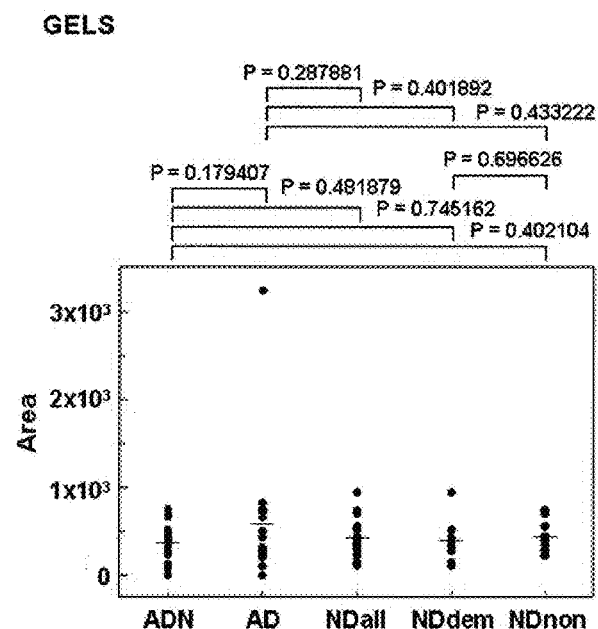

GELS shows as SEQ ID NO: 14 was shown low value in ADN patient, and was shown relatively high value in MCI and AD patients (FIG. 8).

```
Intact protein/peptide
                                               (SEQ ID NO: 13)
001 MAPHRPAPAL LCALSLALCA LSLPVRAATA SRGASQAGAP
    QGRVPEARPN

051 SMVVEHPEFL KAGKEPGLQI WRVEKFDLVP VPTNLYGDFF
    TGDAYVILKT

101 VQLRNGNLQY DLHYWLGNEC SQDESGAAAI FTVQLDDYLN
    GRAVQHREVQ

151 GFESATFLGY FKSGLKYKKG GVASGFKHVV PNEVVVQRLF
    QVKGRRVVRA

201 TEVPVSWESF NNGDCFILDL GNNIHQWCGS NSNRYERLKA
    TQVSKGIRDN

251 ERSGRARVHV SEEGTEPEAM LQVLGPKPAL PAGTEDTAKE
    DAANRKLAKL

301 YKVSNGAGTM SVSLVADENP FAQGALKSED CFILDHGKDG
    KIFVWKGKQA

351 NTEERKAALK TASDFITKMD YPKQTQVSVL PEGGETPLFK
    QFFKNWRDPD

401 QTDGLGLSYL SSHIANVERV PFDAATLHTS TAMAAQHGMD
    DDGTGQKQIW

451 RIEGSNKVPV DPATYGQFYG GDSYIILYNY RHGGRQGQII
    YNWQGAQSTQ

501 DEVAASAILT AQLDEELGGT PVQSRVVQGK EPAHLMSLFG
    GKPMIIYKGG

551 TSREGGQTAP ASTRLFQVRA NSAGATRAVE VLPKAGALNS
    NDAFVLKTPS

601 AAYLWVGTGA SEAEKTGAQE LLRVLRAQPV QVAEGSEPDG
    FWEALGGKAA

651 YRTSPRLKDK KMDAHPPRLF ACSNKIGRFV IEEVPGELMQ
    EDLATDDVML

701 LDTWDQVFVW VGKDSQEEEK TEALTSAKRY IETDPANRDR
    RTPITVVKQG

751 FEPPSFVGWF LGWDDDYWSV DPLDRAMAEL AA
```

Gelsolin Precursor-Derived Peptide GELS

```
                                               (SEQ ID NO: 14)
PVRAATASRGAS
```

(9) Clusterin Precursor-Derived Peptide (CLUS(N-Term SDVP))

CLUS(N-term SDVP) shows as SEQ ID NO: 16 was shown low value in ADN patient, and was shown relatively high value in MCI and AD patients (FIG. 9). Clusterin precursor-derived peptides are two types, and (N-termSDVP) means that the amino acid sequence of N-terminus in peptide is SDVP.

```
Intact protein/peptide
                                               (SEQ ID NO: 15)
001 MMKTLLLFVG LLLTWESGQV LGDQTVSDNE LQEMSNQGSK
    YVNKEIQNAV

051 NGVKQIKTLI EKTNEERKTL LSNLEEAKKK KEDALNETRE
    SETKLKELPG

101 VCNETMMALW EECKPCLKQT CMKFYARVCR SGSGLVGRQL
    EEFLNQSSPF

151 YFWMNGDRID SLLENDRQQT HMLDVMQDHF SRASSIIDEL
    FQDRFFTREP

201 QDTYHYLPFS LPHRRPHFFF PKSRIVRSLM PFSPYEPLNF
    HAMFQPFLEM

251 IHEAQQAMDI HFHSPAFQHP PTEFIREGDD DRTVCREIRH
    NSTGCLRMKD

301 QCDKCREILS VDCSTNNPSQ AKLRRELDES LQVAERLTRK
    YNELLKSYQW

351 KMLNTSSLLE QLNEQFNWVS RLANLTQGED QYYLRVTTVA
    SHTSDSDVPS

401 GVTEVVVKLF DSDPITVTVP VEVSRKNPKF METVAEKALQ
    EYRKKHREE
```

Clusterin Precursor-Derived Peptide CLUS(N-Term SDVP)

```
                                       (SEQ ID NO: 16)
SDVPSGVTEVVVKLFDS
```

(10) Clusterin Precursor-Derived Peptide (CLUS(N-Term RFFT))

CLUS(N-term RFFT) shows as SEQ ID NO: 17 was detected in ADN patient, and was not completely detected in AD patient (FIG. 9). (N-term RFFT) means that the amino acid sequence of N-terminus in peptide is RFFT.

```
Intact protein/peptide
                                       (SEQ ID NO: 15)
001 MMKTLLLFVG LLLTWESGQV LGDQTVSDNE LQEMSNQGSK
    YVNKEIQNAV

051 NGVKQIKTLI EKTNEERKTL LSNLEEAKKK KEDALNETRE
    SETKLKELPG

101 VCNETMMALW EECKPCLKQT CMKFYARVCR SGSGLVGRQL
    EEFLNQSSPF

151 YFWMNGDRID SLLENDRQQT HMLDVMQDHF SRASSIIDEL
    FQDRFFTREP

201 QDTYHYLPFS LPHRRPHFFF PKSRIVRSLM PFSPYEPLNF
    HAMFQPFLEM

251 IHEAQQAMDI HFHSPAFQHP PTEFIREGDD DRTVCREIRH
    NSTGCLRMKD

301 QCDKCREILS VDCSTNNPSQ AKLRRELDES LQVAERLTRK
    YNELLKSYQW

351 KMLNTSSLLE QLNEQFNWVS RLANLTQGED QYYLRVTTVA
    SHTSDSDVPS

401 GVTEVVVKLF DSDPITVTVP VEVSRKNPKF METVAEKALQ
    EYRKKHREE
```

Clusterin Precursor-Derived Peptide CLUS(N-Term RFFT)

```
                                       (SEQ ID NO: 17)
RFFTREPQDTYHYLPFSLPH
```

(11) Eukaryotic Translation Initiation Factor 3 Subunit J-Derived Peptide (EIF3J)

EIF3J shows as SEQ ID NO: 19 was detected in ADN patient, and was not at all or almost detected in MCI, AD, NDall, NDdem, and NDnon patients (FIG. 10).

```
Intact protein/peptide
                                       (SEQ ID NO: 18)
001 MAAAAAAGD SDSWDADAFS VEDPVRKVGG GGTAGGDRWE
    GEDEDEDVKD

051 NWDDDDDEKK EEAEVKPEVK ISEKKKIAEK IKEKERQQKK
    RQEEIKKRLE

101 EPEEPKVLTP EEQLADKLRL KKLQEESDLE LAKETFGVNN
    AVYGIDAMNP

151 SSRDDFTEFG KLLKDKITQY EKSLYYASFL EVLVRDVCIS
    LEIDDLKKIT

201 NSLTVLCSEK QKQEKQSKAK KKKKGVVPGG GLKATMKDDL
    ADYGGYDGGY

251 VQDYEDFM
```

Eukaryotic Translation Initiation Factor 3 Subunit J-Derived Peptide EIF3J

```
                                       (SEQ ID NO: 19)
GVVPGGGLKATMKDDLADYGGYDGG + Oxidation (M)
```

(12) Leucine-Rich Repeat-Containing Protein 27-Derived Peptide (LRC27)

LRC27 shows as SEQ ID NO: 21 was detected in ADN patient, and was not completely detected in AD patient (FIG. 10).

```
Intact protein/peptide
                                       (SEQ ID NO: 20)
001 MEGSSSYEVP SVAAADLEEG AGQTRSLPAT PSKDVHKGVG
    GIIFSSSPIL

051 DLSESGLCRL EEVFRIPSLQ QLHLQRNALC VIPQDFFQLL
    PNLTWLDLRY

101 NRIKALPSGI GAHQHLKTLL LERNPIKMLP VELGSVTTLK
    ALNLRHCPLE

151 FPPQLVVQKG LVAIQRFLRM WAVEHSLPRN PTSQEAPPVR
    EMTLRDLPSP

201 GLELSGDHAS NQGAVNAQDP EGAVMKEKAS FLPPVEKPDL
    SELRKSADSS

251 ENWPSEEEIR RFWKLRQEIV EHVKADVLGD QLLTRELPPN
    LKAALNIEKE

301 LPKPRHVFRR KTASSRSILP DLLSPYQMAI RAKRLEESRA
    AALRELQEKQ

351 ALMEQQRREK RALQEWRERA QRMRKRKEEL SKLLPPRRSM
    VASKIPSATD

401 LIDNRKVPLN PPGKMKPSKE KSPQASKEMS ALQERNLEEK
    IKQHVLQMRE

451 QRRFHGQAPL EEMRKAAEDL EIATELQDEV LKLKLGLTLN
    KDRRRAALTG

501 NLSLGLPAAQ PQNTFFNTKY GESGNVRRYQ
```

Leucine-Rich Repeat-Containing Protein 27-Derived Peptide LRC27

```
                                       (SEQ ID NO: 21)
SSPILDLSESGLCRLEEVFRIPS
```

There have been already quoted, but for the peptides of SEQ ID NO: 2 (NRX2B) to SEQ ID NO: 21 (LRC27), the scatter plots of comparison between ADN, MCI and AD patients, and the scatter plot of comparison between ADN, AD, NDall, NDdem and NDnon patients, and the p-value of t-test in each comparison were showed in FIG. 2, FIG. 4 and FIG. 6 through FIG. 10.

Table 1 shows the list of 12 marker peptides described above and their ROC values for comparison of MCI vs. ADN and AD vs. ADN.

TABLE 1

| Marker peptides | | MCI vs. ADN | | AD vs. ADN | |
| --- | --- | --- | --- | --- | --- |
| Swiss-Prot Entry | Sequence No. | ROC value | MCI was | ROC value | AD was |
| NRX2B | 2 | 0.99 | up | 1 | up |
| THRB (R−) | 4 | 0.854 | down | 0.841 | down |
| THRB (R+) | 5 | 0.94 | up | 0.985 | up |

TABLE 1-continued

| Marker peptides | | MCI vs. ADN | | AD vs. ADN | |
|---|---|---|---|---|---|
| Swiss-Prot Entry | Sequence No. | ROC value | MCI was | ROC value | AD was |
| S26A4 | 7 | 0.925 | up | 0.95 | up |
| COPZ1 | 9 | 0.786 | up | 0.767 | up |
| RARR2 (S−) | 11 | 0.885 | up | 0.914 | up |
| RARR2 (S+) | 12 | 0.95 | up | 0.919 | up |
| GELS | 14 | 0.716 | up | 0.762 | up |
| CLUS (N-term SDVP) | 16 | 0.739 | up | 0.717 | up |
| GLUS (N-term RFFT) | 17 | 0.675 | down | 0.75 | down |
| EIF3J | 19 | 0.748 | down | 0.775 | down |
| LRC27 | 21 | 0.699 | down | 0.755 | down |

Table 1 shows the usefulness of each marker peptide in detection of cognitive impairment (MCI and AD). Using these marker peptides in singly or in combination, using or without using liquid chromatography and/or any other suitable separation methods, directly measuring the abundance in serum using other methods such as mass spectrometry or immunological methods or enzymatic methods, it is possible to distinguish between non-dementia and dementia in neurological disease and diagnose cognitive impairment like AD and MCI. The marker peptide that is not detected in ADN and is detected in MCI, AD, NDall, NDdem and NDnon patients, or vice versa, the marker peptide that is detected in ADN patient and is not detected in MCI, AD, NDall, NDdem and NDnon patients, are also useful for the detection of psychiatric diseases.

Example 2

Example 2. Synthesis of a Marker Peptide, and Preparation of a Marker Peptide Specific Polyclonal Antibody The antigenic peptide was synthesized to prepare the specific antibody that recognizes Neurexin-2-beta precursor-derived peptide NRX2B of SEQ ID NO: 2. The synthetic peptide for coupling to a carrier protein was added the cysteine residue (labeled as C or Cys) in C-terminus. The peptide that was combined with carrier protein (RSGG-NATC(SEQ ID NO: 22)-KLH carrier protein, see below) was mixed with an adjuvant, and the mixture was immunized in rabbit. Total eight times immunizations is performed every 1-2 weeks, and the test blood collection performed twice every 4 weeks, and the antibody titers were measured by enzyme immunoassay (EIA). After three months from the start of the immunization, the whole blood was collected from rabbit and the antiserum was obtained, furthermore the purification of the specific antibody was performed using the peptide column that antigen peptide was bound as ligand.

The sequence of synthetic antigen peptide for preparation of peptide specific antibody is shown below.

RSGGNAT + Cys (SEQ ID NO: 22)

Example 3

Example 3. Preparation of Antibody-Beads (1) Method (1-1) Preparation of Antibody, and Binding to Magnetic-Beads The antibody solution, 1 mg of the antibody (anti-NRX2B antibody, Rabbit IgG) that specifically recognizes the peptide of amino acid sequence expressed by SEQ ID NO: 22 was dissolved with 3 ml of 0.1 M MES. After washing 1 ml (10 mg beads) of the magnetic-beads (Magnosphere MS300/carboxyl, JSR Corporation) by using 0.1 M MES, the magnetic-beads were mixed with the antibody solution and were gently shaken for 30 min at room temperature.

(1-2) Cross-Linking of Antibody and Magnetic-Beads

400 µl of EDC solution (10 mg/ml 1-ethyl-3-(3-dimethylaminopropyl) carbodiimide hydrochloride in 0.1M MES) was added in antibody-beads solution and was suspended gently for 3 hours to bind antibody with beads by covalent bond.

(1-3) Blocking 1 ml of 200 mM ethanolamine (pH8.0) was added to wash beads, and further 1 ml of 200 mM ethanolamine (pH8.0) was added and was shaken gently for 1 hours at room temperature to block amine groups.

(1-4) Washing

After removal of 200 mM 200m M ethanolamine (pH8.0), the beads were washed three times by 1 ml of TBST solution (25 mM Tris-HCl (pH7.2) containing 0.15M NaCl and 0.05% Tween 20).

(1-5) Storage

After suspending the beads by adding with 1 ml of TBST solution, and stored at 4° C.

Example 4

Example 4. The Proof by immunoMS Method that the Peak of m/z 1,488 in Patient Serum Detected by 2D-LC-MALDI-TOF-MS is NRX2B (1) Methods As the control for comparison, stable isotope-labeled NRX2B synthetic peptide (12C and 13C5 of V has been replaced by 15N and 14N) greater than mass of NRX2B was used. The mass difference between NRX2B and its stable isotope peptide is 6 u. Both the endogenous peptide and the stable isotope-labeled peptide are captured by anti-NRX2B antibody. 1 µl of 200 fmol/µl stable isotope-labeled NRX2B synthetic peptide was added in 25 µl of each of patient serum in AD and MCI, and incubated for 10 min at 4° C. Then, 475 µl of 0.1% trifluoroacetic acid (TFA) was added and boiled for 5 min at 100° C. After centrifugation for 15 min at 14,000×g, 500 µl of 100 mM Tris-HCl buffer (pH 7.5) containing 0.3 M NaCl and 0.2% n-octyl glycoside was added in supernatant as peptide solutions. 20 µl of anti-NRX2B antibody-beads created in Example 3 was added in the peptide solutions, and was shaken gently for 2 hours. Then, after standing for 1 min on the magnetic stand, the supernatant was removed. 1 ml of 50 mM Tris-HCl buffer (pH 7.5) (TBS) containing 0.15 M NaCl and 0.1% n-octyl glycoside was added, and was shaken gently for 10 min. After standing for 1 min on the magnetic stand, the supernatant was removed. In addition, after adding 500 µl of TBS, and standing for 1 min on the magnetic stand, the supernatant was removed. This procedure was repeated three times. Furthermore, after adding 500 µl of 50 mM ammonium carbonate, and standing for 1 min on the magnetic stand, the supernatant was removed. This procedure was repeated three times. 50 µl of 2-propanol: H2O: formic acid (4:4:1) solution was added, and was stood for 10 min, and then after standing for 1 min on the magnetic stand, the filtrate was recovered. This procedure was repeated twice. The filtrates were completely dried using vacuum centrifuge. Then, 20 µl of 0.095 TFA containing 5% acetonitrile was added and was re-dissolved by sonication. The peptides were concentrated using C18 pipette tip (PerfectPure C-18 Tip, Eppendorf), and were spotted on MALDI target plate (MTP AnchorChip™ 600/384 plate, BRUKER DALTONICS) by eluting from C18 pipette tip, and then the peptides were analyzed using MALDI TOF mass spectrometer (AXIMA CFRplus, SHIMADZU).

(2) Results

Figure 11:
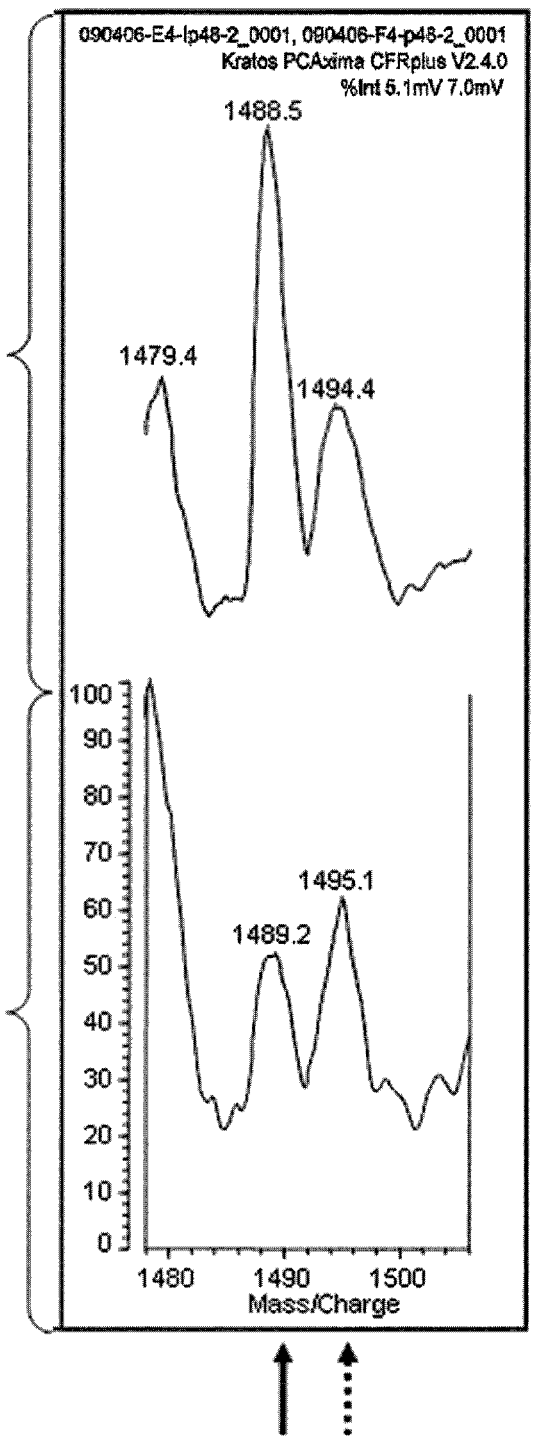

FIG. 11 shows the result of the mass spectrum of NRX2B peptide detected from the patient serum in AD and MCI using the above method. FIG. 11 A) shows the overall mass spectrum, and FIG. 11 B) shows the enlarged view of the arrow parts in FIG. 11 A). The signal indicated by dashed arrows in FIG. 11 B) is stable isotope-labeled NRX2B synthetic peptide that was spiked, and the signal indicated by solid arrows is endogenous NRX2B peptide. The observed mass value was within the measurement error of the expected value. And also the mass difference between endogenous NRX2B peptide and its stable isotope-labeled peptide was 6 u. Therefore, it was demonstrated that the trapped peptide is NRX2B.

In this experiment, NRX2B which is the peptide marker was detected from serum by using immunoMS method that developed originally by present inventors, and it could be shown that it is possible to distinguish between AD and MCI patients from ADN. At the same time, in this experiment, it has also shown that the specific antibody against NRX2B is useful in detecting its peptide marker. In addition, it also shows that immunological detection method could be effective against the peptide or protein comprised in the amino acid sequence of NRX2B using the specific antibody against NRX2B. In addition, in this experiment, it was determined by using the specific antibodies that recognize one peptide marker, but the combination of biomarkers specific antibodies that recognize other peptides that were found in Example 1, is expected to further increase the accuracy of diagnosis of the pathosis.

INDUSTRIAL APPLICABILITY

As cognitive impairment including mild cognitive impairment and Alzheimer disease and cognitive impairment and non-psychiatric disease can be detected by using the biomarkers disclosed in the present invention, the invention is applicable to the use in the field of medical diagnosis including that of diagnostic agents.

SEQUENCE LISTING

09P01007_Sequence.txt

---

The invention claimed is:

1. A method for detecting a biomarker for mild cognitive impairment or Alzheimer's disease in a human subject at a preclinical stage, comprising:
   (a) obtaining a serum sample from the human subject;
   (b) measuring at least one biomarker in the serum sample, using a detection method selected from the group consisting of two-dimensional liquid chromatography (2D-LC)-MALDI TOF-MS and LC-MS/MS, wherein the serum sample of said (b) is an acid-treated sample or an ultrafiltered sample after acid-treatment,
   wherein the at least one biomarker is at least one peptide selected from the group consisting of:
   prothrombin precursor derived peptide THRB(R−) consisting of the amino acid sequence of SEQ ID NO: 4, and
   prothrombin precursor-derived peptide THRB(R+) consisting of the amino acid sequence of SEQ ID NO: 5; and
   (c) diagnosing the human subject with a mild cognitive impairment or Alzheimer's disease based on the level of the at least one biomarker, if:
   (i) the peptide having the amino acid sequence of SEQ ID NO:4 is absent or decreased in the serum sample, as compared to the amount of the peptide having the amino acid sequence of SEQ ID NO:4 in biological material of subjects not suffering from mild cognitive impairment or Alzheimer's disease; and/or
   (ii) the peptide having the amino acid sequence of SEQ ID NO:5 is present or increased in the serum sample, as compared to the amount of the peptide having the amino acid sequence of SEQ ID NO:5 in biological material of subjects not suffering from mild cognitive impairment or Alzheimer's disease.

2. The method according to claim 1, using a detection method that is two-dimensional liquid chromatography (2D-LC)-MALDI TOF-MS.

3. The method according to claim 1, using a detection method that is LC-MS/MS.

* * * * *